US010226217B2

(12) United States Patent
Dubin et al.

(10) Patent No.: US 10,226,217 B2
(45) Date of Patent: Mar. 12, 2019

(54) SYSTEM, METHOD AND COMPUTER PROGRAM PRODUCT FOR PHYSIOLOGICAL MONITORING

(71) Applicant: Tyto Care Ltd., Netanya (IL)

(72) Inventors: Uri Dubin, Haifa (IL); Elad Lachmanovich, Modi'in (IL); Dov Danon, Kiryat Ata (IL); Eyal Bychkov, Hod Hasharon (IL)

(73) Assignee: TYTO CARE LTD., Netanya (IL)

( * ) Notice: Subject to any disclaimer, the term of this patent is extended or adjusted under 35 U.S.C. 154(b) by 51 days.

(21) Appl. No.: 15/332,090

(22) Filed: Oct. 24, 2016

(65) Prior Publication Data

US 2017/0112439 A1 Apr. 27, 2017

Related U.S. Application Data

(60) Provisional application No. 62/244,796, filed on Oct. 22, 2015.

(51) Int. Cl.
*A61B 5/00* (2006.01)
*G06F 19/00* (2018.01)
(Continued)

(52) U.S. Cl.
CPC ............ *A61B 5/684* (2013.01); *A61B 5/0013* (2013.01); *A61B 5/0077* (2013.01);
(Continued)

(58) Field of Classification Search
None
See application file for complete search history.

(56) References Cited

U.S. PATENT DOCUMENTS 8,265,907 B2 * 9/2012 Nanikashvili ......... A61B 5/1112
600/301
8,364,242 B2 * 1/2013 Li ......................... A61B 5/062
382/128
(Continued)

OTHER PUBLICATIONS

3M Littmann, Redefining what a stethoscope can do for you, p. 1-8, 2013.

*Primary Examiner* — Soo Shin
(74) *Attorney, Agent, or Firm* — Browdy and Neimark, PLLC

(57) ABSTRACT

A system for measuring physiological parameters, including: a portable measurement system, operable to acquire physiological measurement from an examined body location; an external camera operable to capture visible light, oriented toward the examined body location; a synchronization module, operable to receive a triggering indication, and in response to the triggering indication to associate to the physiological measurement a positioning image captured by the camera, the positioning image including at least a part of the portable measurement system adjacent to the examined body location; and a communication module operable to obtain the physiological measurement and the positioning image, and to transmit to a remote system: a physiological measurement record based on the physiological measurement, an orientation image based on the positioning image, and including at least a part of the portable measurement system adjacent to the examined body location, and association data associating the orientation image and the physiological measurement record.

70 Claims, 17 Drawing Sheets

(51) Int. Cl.
*A61B 7/00* (2006.01)
*A61B 8/00* (2006.01)
*A61B 8/14* (2006.01)
*A61B 7/04* (2006.01)
*A61B 5/026* (2006.01)
*G16H 40/63* (2018.01)

(52) U.S. Cl.
CPC ............ *A61B 5/7285* (2013.01); *A61B 5/743* (2013.01); *A61B 5/7475* (2013.01); *A61B 7/003* (2013.01); *A61B 7/04* (2013.01); *A61B 8/14* (2013.01); *A61B 8/4416* (2013.01); *A61B 8/4427* (2013.01); *G06F 19/00* (2013.01); *G16H 40/63* (2018.01); *A61B 5/026* (2013.01); *A61B 2576/00* (2013.01)

(56) References Cited

U.S. PATENT DOCUMENTS

| | | | |
|---|---|---|---|
| 9,015,008 B2* | 4/2015 | Geva | A61B 5/1112 702/188 |
| 2006/0039105 A1 | 2/2006 | Smith et al. | |
| 2008/0180538 A1* | 7/2008 | Jung | G06K 9/3241 348/222.1 |
| 2013/0216114 A1* | 8/2013 | Courtney | A61B 5/0066 382/128 |
| 2013/0238106 A1 | 9/2013 | Ellis et al. | |
| 2013/0245456 A1 | 9/2013 | Ferguson et al. | |
| 2013/0338447 A1* | 12/2013 | Gilad-Gilor | A61B 5/0077 600/300 |
| 2016/0135696 A1* | 5/2016 | Cobbett | A61B 5/0205 600/479 |
| 2016/0287172 A1* | 10/2016 | Morris | A61B 5/04085 |
| 2017/0236281 A1* | 8/2017 | Dacosta | G06T 7/0016 382/128 |

* cited by examiner

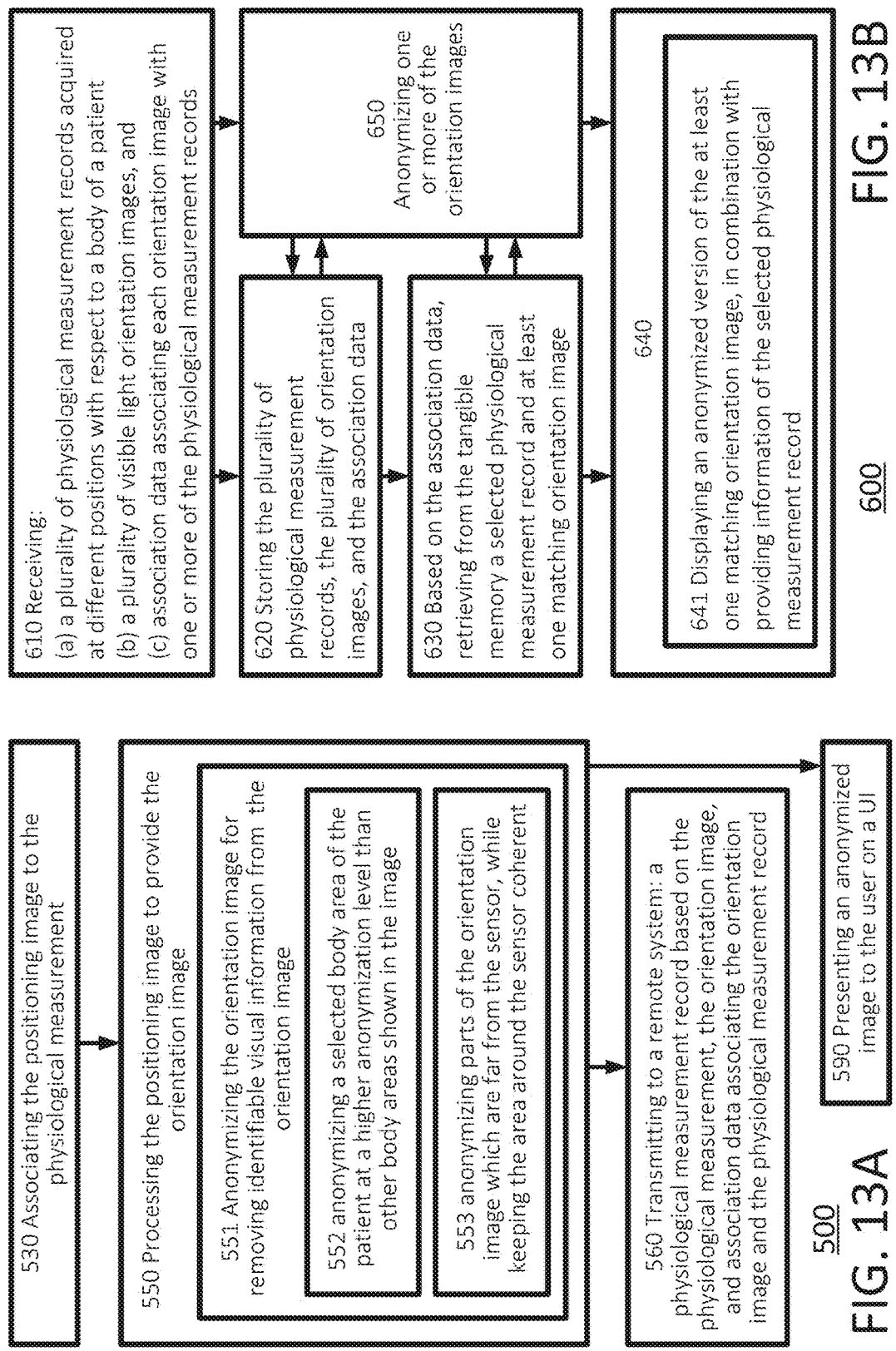

1810 Processing at least one visible light image showing a body of a patient and a portable measurement system to determine a location of the portable measurement system in the at least one image

↓

1820 Initiating a new phase of a physiological measurement of the patient by the portable measurement system, upon a condition in which the location fulfils a proximity criterion with respect to a predetermined examination location

1800     FIG. 18

2010 Acquiring a reference image which includes at least a part of a body of a patient (acquired by an external camera)

↓

2020 Obtaining at least one examination location which is defined with respect to a reference image which comprises at least a part of a body of a patient

↓

2030 Determining positioning parameters for the portable measurement system, based on the at least one examination location

↓

2040 Controlling execution of a physiological measurement of the patient by the portable measurement sensor, based on the positioning parameters

2000     FIG. 20

SYSTEM, METHOD AND COMPUTER PROGRAM PRODUCT FOR PHYSIOLOGICAL MONITORING

FIELD

The invention related to systems, methods, and computer program products for physiological monitoring and for physiological measurement.

BACKGROUND

Various portable measurement systems are known in the art, of which several portable measurement systems can transmit the results of the physiological measurements to a distanced location. For example, Electronic Stethoscope Littmann Model 3200 by 3M can transmit digitally sampled sounds via Bluetooth communication to another system. However, such prior art systems do not provide to the system at the remote locations (and hence possibly to a medical expert or to a specializing diagnosis system) indication on where was the physiological measurement system with respect to the body of the patient at the time of measurement. Furthermore, such prior art systems do not enable controlling of the physiological measurement based on where the physiological measurement system is positioned with respect to the body of the patient and based on instructions of a medical expert at a remote location.

Further limitations and disadvantages of conventional, traditional, and proposed approaches will become apparent to one of skill in the art, through comparison of such approaches with the subject matter of the present application as set forth in the remainder of the present application with reference to the drawings.

GENERAL DESCRIPTION

According to an aspect of the invention, there is provided a system for measuring physiological parameters of a patient, the system including:
  a. a portable measurement system, operable to acquire physiological measurement from an examined body location of the patient;
  b. an external camera operable to capture visible light, oriented toward the examined body location;
  c. a synchronization module, operable to receive a triggering indication, and in response to the triggering indication to associate to the physiological measurement a positioning image captured by the external camera, the positioning image including at least a part of the portable measurement system adjacent to the examined body location; and
  d. a communication module operable to obtain the physiological measurement and the positioning image, and to transmit to a remote system: (i) a physiological measurement record which is based on the physiological measurement, (ii) an orientation image which is based on the positioning image, the orientation image including at least a part of the portable measurement system adjacent to the examined body location, and (iii) association data associating the orientation image and the physiological measurement record.

According to an aspect of the invention, there is provided a physiological monitoring system, the system including:
  a. a communication module operable to receive: (i) a plurality of physiological measurement records of a plurality of physiological measurements acquired at different positions with respect to a body of a patient, (ii) a plurality of visible light orientation images, each of the plurality of visible light orientation images being indicative of a location of a portable measurement system with respect to the body of the patient, and (iii) association data associating each orientation image with a corresponding physiological measurement record out of the plurality of physiological measurement records;
  b. a tangible memory operable to store the plurality of physiological measurement records, the plurality of orientation images, and the association data;
  c. a processor, configured and operable to process the association data and to retrieve from the tangible memory, based on results of the processing, a selected physiological measurement record and at least one matching orientation image; and
  d. a user interface output configured to display the at least one matching orientation image in combination with providing information of the selected physiological measurement record.

According to an aspect of the invention, there is provided a physiological monitoring system, the system including:
  a. a portable measurement system, operable to acquire physiological measurement of the patient;
  b. an external camera operable to capture visible light, oriented toward the examined body location;
  c. a processor, operable to: (a) process at least one image acquired by the external camera to determine a location of the portable measurement system in the image at least one image; and (b) initiate a change in the physiological measurement of the portable measurement system upon a condition in which the location fulfils a proximity criterion with respect to a predetermined examination location.

According to an aspect of the invention, there is provided a system for controlling measuring of physiological parameters of a patient, the system including:
  a. a communication interface operable to receive at least one examination location, wherein the at least one examination location is defined with respect to a reference image which includes at least a part of a body of a patient;
  b. a processor, operable to process the at least one examination location, and to determine positioning parameters for the portable measurement system based on a result of the processing; and
  c. a controller, operable to control execution of a physiological measurement of the patient by a portable measurement sensor, based on the positioning parameters; wherein the reference image is a visible light image acquired by an external camera which is external to the portable measurement system.

According to an aspect of the invention, there is provided a method for measuring physiological parameters of a patient, the method including:
  a. associating a positioning image to a physiological measurement acquired from an examined body location of the patient by a portable measurement system; the positioning image being an image captured by an external visible light camera which is oriented toward the examined body location, which includes the portable measurement system adjacent to the examined body location; and
  b. transmitting to a remote system: (i) a physiological measurement record which is based on the physiological measurement, (ii) an orientation image which is based on the positioning image and which includes the portable measurement system adjacent to the examined body location, and (iii) association data associating the orientation image and the physiological measurement record.

According to an aspect of the invention, there is provided a computer-implemented method for physiological monitoring, the method including:
a. receiving: (i) a plurality of physiological measurement records of a plurality of physiological measurements acquired at different positions with respect to a body of a patient, (ii) a plurality of visible light orientation images, each of the plurality of orientation images being indicative of a location of a portable measurement system with respect to the body of the patient, and (iii) association data associating each orientation image with a corresponding physiological measurement record out of the plurality of physiological measurement records;
b. storing on a tangible memory: the plurality of physiological measurement records, the plurality of orientation images, and the association data;
c. based on the association data, retrieving from the tangible memory a selected physiological measurement record and at least one matching orientation image; and
d. displaying the at least one matching orientation image in combination with providing information of the selected physiological measurement record.

According to an aspect of the invention, there is provided a computer-implemented method for physiological monitoring, the method including:
a. processing at least one visible light image showing a body of a patient and a portable measurement system to determine a location of the portable measurement system in the at least one image; and
b. initiating a new phase of a physiological measurement of the patient by the portable measurement system, upon a condition in which the location fulfils a proximity criterion with respect to a predetermined examination location.

According to an aspect of the invention, there is provided a computer-implemented method for physiological monitoring, the method including:
a. obtaining at least one examination location which is defined with respect to a reference image which comprises at least a part of a body of a patient;
b. determining positioning parameters for the portable measurement system, based on the at least one examination location; and
c. controlling execution of a physiological measurement of the patient by the portable measurement sensor, based on the positioning parameters; wherein the reference image is a visible light image acquired by an external camera external to the portable measurement system.

According to an aspect of the invention, there is provided a non-transitory computer-readable medium for physiological monitoring, including instructions stored thereon, that when executed on a processor, perform the steps of:
a. obtaining: (i) a plurality of physiological measurement records of a plurality of physiological measurements acquired at different positions with respect to a body of a patient, (ii) a plurality of visible light orientation images, each of the plurality of orientation images being indicative of a location of a portable measurement system with respect to the body of the patient, and (iii) association data associating each orientation image with a corresponding physiological measurement record out of the plurality of physiological measurement records;
b. storing on a tangible memory: the plurality of physiological measurement records, the plurality of orientation images, and the association data;
c. based on the association data, retrieving from the tangible memory a selected physiological measurement record and at least one matching orientation image; and
d. displaying the at least one matching orientation image in combination with providing information of the selected physiological measurement record.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 13A and 13B are flow charts illustrating examples of anonymization in the methods of FIGS. 8 through 12, in accordance with the presently disclosed subject matter;

FIG. 18 is a flow chart illustrating an example of a computer-implemented method for physiological monitoring, in accordance with the presently disclosed subject matter;

FIG. 20 is a flow chart illustrating an example of a computer-implemented method for physiological monitoring, in accordance with the presently disclosed subject matter.

Figure 1:
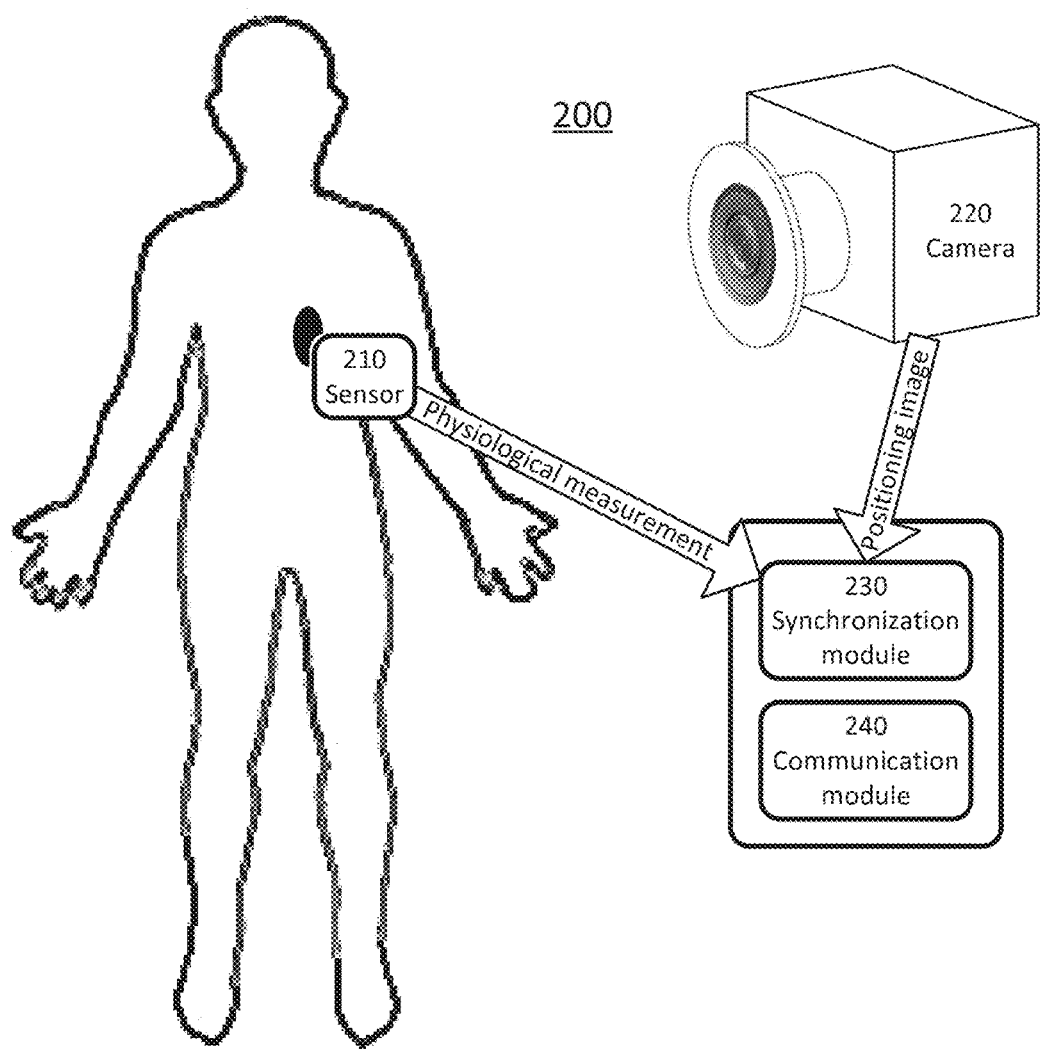
FIGS. 1, 2, 3, and 4 are functional block diagrams illustrating examples of systems for measuring physiological parameters of a patient, in accordance with the presently disclosed subject matter.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "processing", "computing", "determining", "generating", "selecting", or the like, include action and/or processes of a computer that manipulate and/or transform data into other data, said data represented as physical quantities, e.g. such as electronic quantities, and/or said data representing the physical objects. The terms "computer", "processor", and "controller" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

FIG. 1 is a functional block diagram illustrating an example of system 200 for measuring physiological parameters of a patient, in accordance with the presently disclosed subject matter. While not necessarily so, system 200 may be designed to be operated by a non-professional operator (or a semi-professional operator), such as the patient herself, a family member of the patient, or another operator which is not specifically trained to undertake the respective one or more physiological measurements offered by the system.

The term "physiological parameter" which is well accepted in the art, should be construed in a non-limiting way to include any vital sign of the patient, and any other parameter representing a physiological characteristic of a patient. The patient may be any person (or animal) whose physiological parameters are to be measured, whether if for medical use or for any other use (e.g. estimating effectivity of physical training, and so on).

For example, system 200 may be used to measure any combination of one or more of the following physiological parameters of the patient: body temperature, blood pressure, blood saturation, electrocardiogram (ECG) measurements, audio signals (e.g. of the heart operations or of the lungs), ultrasound signals (e.g. of the heart, of the intestines, etc.), acoustic measurements, body tissue electrical resistance, hardness of body tissues, and so on.

System 200 includes portable measurement system 210, which is operable to acquire physiological measurement from an examined body location of the patient. The physiological measurement may be a direct measurement of the physiological parameter, but may also be measurement of a physiological signal (i.e. signal which originates in the body of the patient, or which is based on a signal originating in the body of the patient) which can be processed to provide the physiological parameter. For example, portable measurement system 210 may acquire measurements of electric currents from the examined body location, and these currents may later be processed (by a processor of system 200 or by an external system) to provide a physiological parameter such as local body fat percentage.

The examined body location is a superficial location on the body of the patient (i.e. on the skin, or otherwise on one or more external features of the body, such as the eyes, the fingernails, etc.) where the physiological measurement is acquired by portable measurement system 210. The examined body location may be the part of the organ which is being measured (e.g. if the skin is being measured), or a superficial location which is proximate to the measured organ (e.g. if deeper organs are measured, such as audial examination of the lungs, etc.). The term "superficial" is well accepted in anatomy, for describing locations which are near the outer surface of the organism, such as the skin. The opposite of superficial is "deep", or "visceral".

It is noted that portable measurement system 210 is located outside the body of the patient when acquiring the physiological measurement. Nevertheless, in some cases some parts of portable measurement system 210 may enter the body of the patient (e.g. a needle penetrating the skin and/or a blood vessel, a sensor entering a body orifice such as the ear or the mouth, and so on). Even in such cases, the greater part of portable measurement system 210 is located outside the body at the time of measurement.

It is noted that portable measurement system 210 may include one or more physiological measurement sensors 211, as well as additional components such as one or more of the following modules: communication module 212, power source 213, processor 214, casing 215, and so on. It is possible to use a system 200 which includes more than one portable measurement system 210, in which case the following description pertains to one of these portable measurement systems 210 (or to more than one). For the simplicity of discussion, portable measurement system 210 is also referred to as "sensor 210", even though it may include additional components as discussed above.

It is noted that the physiological measurement may be a location-sensitive physiological measurement, e.g. a physiological measurement whose medical interpretation necessitate information of location of measurement. That is, in order to use the results of the physiological measurement (e.g. for diagnosis, screening or evaluation of the patient, or of its symptom or condition), it is necessary to interpret the results based on the location in which the physiological measurement was executed.

In many types of physiological measurement, the body location from which the physiological measurement is acquired may significantly change the way the results of the measurements are interpreted. For example, blood pressure which is considered normal when measured at the upper arm may be considered alarming if measured at the lower arm. In another example, auscultatory sound sample of the right lung and of the left lung may require different treatment to the patient (especially if combined with the result of other location-specific measurement such as temperature measurements). In yet another example, measuring hardness of the belly in some belly locations may be indicative of inflammation of the appendix (or other gastrointestinal condition), it may be meaningless in other location on the belly.

It is noted that providing the orientation image which provides a location context for a physiological measurement—and/or making sure that the physiological measurement was executed in a correct location—can greatly affect the effectively of the physiological measurement. For example, measuring ECG (or other types of physiological measurements) in incorrect locations can result in missing certain cardiac conditions which can be detected by correctly positioned sensors (as facilitated by system 200). For example, measuring ECG (or other types of physiological measurements) in incorrect locations can result in false alarms (the likelihood of which can be greatly reduced when properly positioning the sensors, as facilitated by system 200). System 200 also facilitate proper and exact diagnosis of symptom (e.g. determining in which lung the patient suffers from a breathing condition). Other advantages of system 200 over prior art system can be easily understood by those skilled in the art.

System 200 further includes camera 220, synchronization module 230 and communication module 240, in order to provide location information together with the results of the physiological measurement, thereby providing whoever interprets the measurement results additional information which is indicative of the examined body location in which the measurement was taken. Camera 220 (also referred to as "external camera 220") is external to sensor 210, in the sense that it is physically separated from sensor 210. External camera 220 is preferably movable irrespectively of sensor 210. Camera 220 is operable to capture visible light, and to generate images based on light it captures. Camera 220 may also be sensitive to other parts of the electromagnetic spectrum near the visible spectrum (e.g. to infrared radiation, such as near IR radiation), but this is not necessarily so. Camera 220 may be sensitive to the entire visible spectrum (e.g. a commercial-off-the-shelf camera, such as a DSLR camera, a smartphone camera, a webcam camera), or only to a part of it.

External camera 220 is oriented toward the examined body location, in at least some of the time in which system 200 operates. As a camera, camera 220 is operable to acquire images, either as still images or as video, or both. Especially, camera 220, when oriented toward the examined body location (as described), is operable to acquire one or more images which includes sensor 210 (i.e. showing all of sensor 210 or parts of it) when sensor 210 is adjacent to the examined body location.

One (or more) of the images captured by camera 220 is used as a positioning image, which includes sensor 210 adjacent to the examined body location. The positioning image also include parts of the body of the patient, which enable to recognize a location of sensor 210 with respect to the examined body location. The body parts included in the positioning image may include the examined body location, but this is not necessarily so. For example, the examined body location itself may be hidden by sensor 210 (especially if the latter touches the body of the patient), but the positioning of sensor 210 with respect to the body may be evident from nearby parts of the body with are shown in the positioning image.

Throughout the present disclosure, certain images are described as including the portable measurement system, body parts of the patient, or other image content. The term "including" in the context of inclusion in an image, in the context of the present disclosure, means that the respective image shows the relevant object (i.e. the image includes visual representation of light which arrives from the object to the camera and which is collected by the camera). It is noted that the image may include an object (e.g. sensor, body part), even if only a part of that object is shown in the image. Other parts of the object which is included in the image may, for example, be hidden by other objects, may exclude the borders of the image, or may simply face away from the camera.

Optionally, the positioning image may be acquired while sensor 210 performs the physiological examination for acquiring the physiological measurement. However, this is not necessarily so, and camera 220 may also acquire the positioning image before or after the physiological measurement is executed (e.g. if sensor 210 is held in place during the measurement, and before or after the measurement). It is noted that if camera 220 acquires more than one image, the selection of which image is later used as the positioning image may be performed by camera 220, and/or by other component of system 200 (e.g. by synchronization module 230).

Synchronization module 230 is operable to receive a triggering indication, and in response to the triggering indication to associate the positioning image captured by camera 220 to the physiological measurement acquired by portable measurement system 210. Optionally, synchronization module 230 may be integrated with portable measurement system 210 (where integrated in the present context means encased in a single casing and sharing one or more components, such as processor, power source and/or communication module). Optionally, synchronization module 230 may be integrated with camera 220. Optionally, synchronization module 230 may be separated from portable measurement system 210 and from camera 220.

The triggering indication may be:
a. An indication of a triggering by a user, received from user interface 280;
b. An indication received from another system (e.g. from a remote computer which manages the physiological examination);
c. An indication from a sensor of system 200 (or of another system), which indicates that a triggering even occurred. For example, the sensor may indicate that the portable measurement system 210 touches a skin of the patient for over a second, or that it senses temperature of at least 35° C.

The association of the positioning image to the physiological measurement includes creating digital association data which unambiguously identifies the orientation image and the physiological measurement. For example, such data may include embedding the same identification number (or alphanumeric string) in the physiological measurement record and in the orientation image.

The association may include storing with (or in) the physiological measurement association data which identifies the positioning image. The association may include storing with (or in) the positioning image association data which identifies the physiological measurement (or parts of the physiological measurement). The association may include generating (or updating) a data structure which is stored independently of images acquired by camera 220, and independently of physiological measurement data acquired by sensor 210.

System 200 also includes communication module 240, which is operable to obtain the physiological measurement and the positioning image. Communication module 240 may receive the positioning image from camera 220, or from synchronization module 230, or from portable measurement system 210 (e.g. if synchronization module 230 is integrated to sensor 210). Communication module 240 may receive the physiological measurement from portable measurement system 210, or from synchronization module 230, or from camera 220 (e.g. if synchronization module 230 is integrated to camera 220).

Communication module 240 is further operable to transmit to a remote system (e.g. system 300, system 400):
a. a physiological measurement record which is based on the physiological measurement;
b. an orientation image which is based on the positioning image; and
c. association data associating the orientation image and the physiological measurement record.

Figure 2:
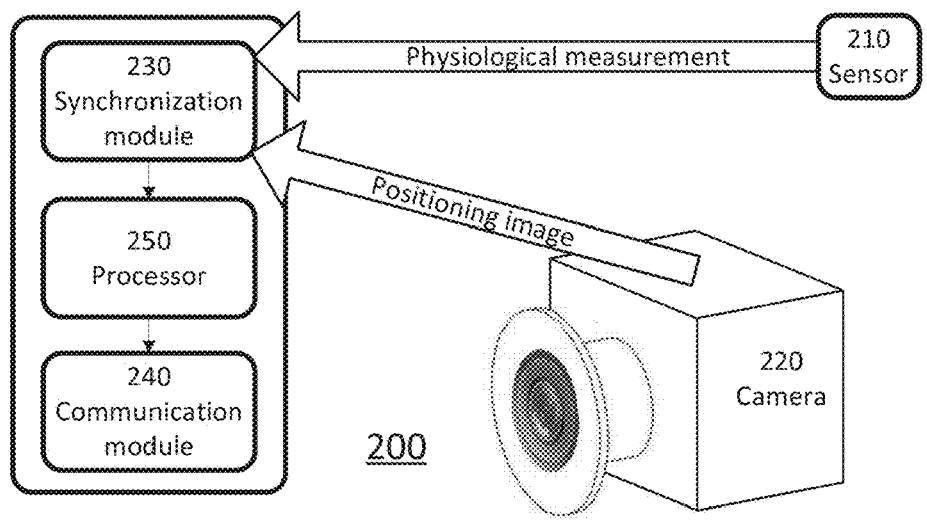

The physiological measurement record may include the entire physiological measurement acquired by portable measurement system 210 from the examined body location, or only part of it, or include processed data which is based on the physiological measurement (or part of it). As exemplified in FIG. 2, which is a functional block diagram illustrating an example of system 200 in accordance with the presently disclosed subject matter, system 200 may include processor 250 which is operable to receive some or all of the physiological measurement acquired by portable measurement system 210 from the examined body location, and to process it. The processing may include various processing algorithms, such as (but not limited to): selecting parts of the physiological measurements (and discarding other parts), improving a quality of the sample, adding metadata, combining with another physiological measurement, modifying based on another physiological measurement (or on other data such as time and geographic location), and so on and so forth.

For example, the physiological measurement may include a sound sample from lungs of the patient. Prior to sending the physiological measurement, processor 250 may analyze the sound sample to detect which parts are recorded when sensor 210 is not properly located (and are therefore of no value for the medical expert), and remove these parts from the sound sample. Later, processor 250 may process the remaining sound sample in order to add metadata, indicating times in which the patient was instructed by system 200 to cough.

The orientation image may be the entire positioning image as acquired by the camera—or part of that image, but may also include another image which was generated based on a processing of the positioning image (e.g. by processor 250). Like the positioning image, the orientation image (or images) transmitted by communication module 240 to the external system show sensor 210 adjacent to the examined body location, and further include parts of the body of the patient, which enable to recognize a location of sensor 210 with respect to the examined body location. The orientation image includes at least a part of the portable measurement system adjacent to the examined body location. Processor 250 may process the positioning image in order to add or remove data, in order to add metadata, and so on.

System 200 (and especially sensor 210) may be used for various types of physiological measurements. For example, portable measurement system 210 may include a microphone which is operable to acquire the physiological measurement which includes internal sounds of the body of the patient (e.g. sounds of one or both lungs of the patient, of the heart, of the uterus, of the intestines, and so on). Referring to the examples of the lungs, knowing where the microphone is located with respect to the body of the patient may enable to identify a location of a physical symptom in the lungs.

It is noted that system 200 may optionally also be used to detect ultrasonic sound waves (e.g. for ultrasonic imaging).

For example, portable measurement system 210 may include an ultrasonic transducer (e.g. a piezoelectric transducer) which is operable to acquire the physiological measurement which includes ultrasonic sound waves reflected from a body of the patient. Processor 250 may be operable, in such case, to execute the calculations involved in processing the data collected by the ultrasonic transducer, in order to provide a visual representation of the examined location. Optionally, processor 250 may also be configured to control the electrical currents sent to the transducer probe to emit ultrasonic sound waves.

Optionally, portable measurement system 210 may include a blood flow sensor which is operable to acquire the physiological measurement which is indicative of at least one blood flow parameter. Such parameters may include, for example, systolic blood pressure, diastolic blood pressure, oxygen saturation, and so on.

Different kinds of systems may serve as the remote system 300 to which system 200 transmits data (e.g. system 400), depending on the way the information gathered and processed by system 200 is to be used. For example, the information gathered and processed by system 200 may be reviewed by a trained medical expert, it may be automatically processed by a software system, it may be stored for later use in a data base, and so on. For example, the remote system to which system 200 transmits data (e.g. system 400) may be a server, a personal computer, a smart phone, a television set, a non-volatile storage system, and so on. While not necessarily so, the remote system to which system 200 transmits data (e.g. system 400) may be operable to receive from many systems 200 information of many different patients.

It is noted that any combination of one to four of components 210, 220, 230, 240 and 250 (which do not include both sensor 210 and camera 220) may be integrated into a computerized system having other capabilities (such as a smartphone, a personal computer or a laptop computer, a digital camera, and so on). As aforementioned, camera 220 is external to sensor 210, and therefore this two units are not integrated into a single casing.

Figure 3:
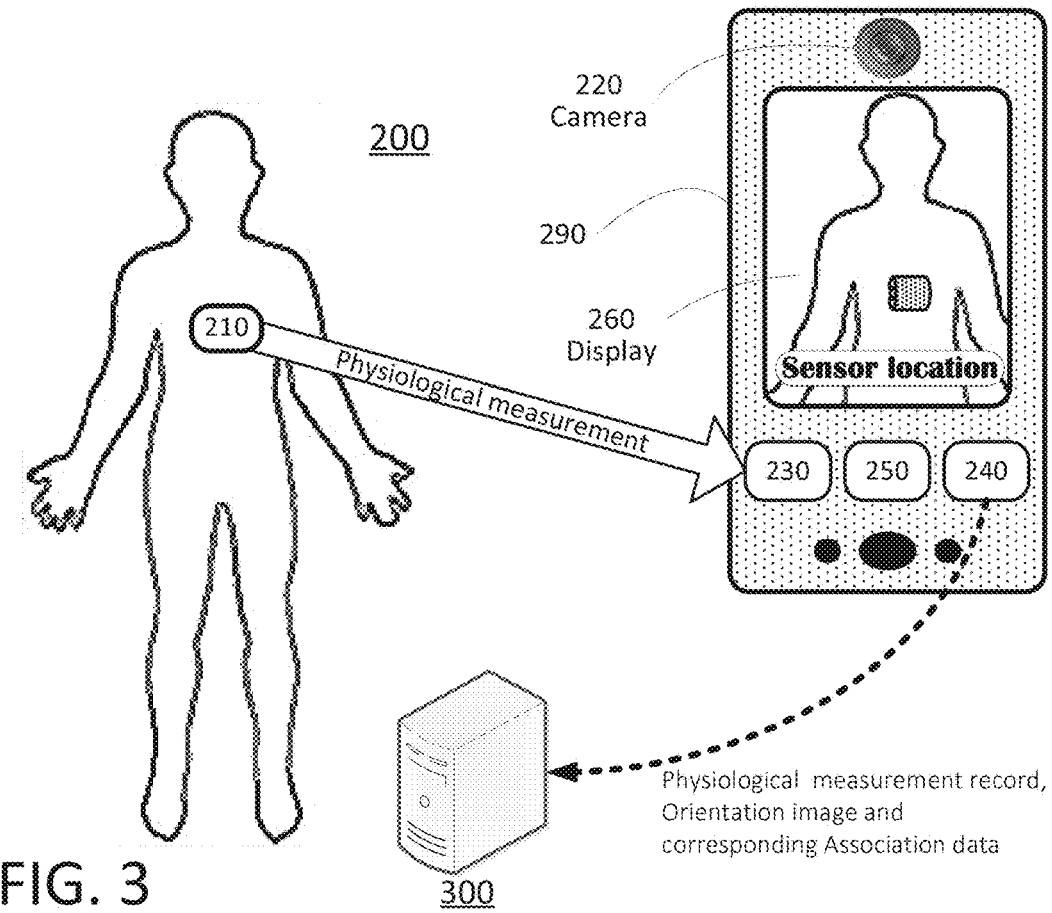

For example, using a dedicated portable measurement system 210, the camera of a smartphone (or another portable computer such as a tablet computer, denoted 290) may be used as camera 220, the processor of the smartphone may be used as synchronization module 230 (and possibly also as processor 250), and a communication module of the smartphone (e.g. the cellular communication module, the Wi-Fi communication module, or the Bluetooth communication module) may be used as communication module 240. An example for such a configuration is illustrated in FIG. 3, which is a functional block diagram illustrating an example of system 200 for measuring physiological parameters of a patient, in accordance with the presently disclosed subject matter. Similar implementations could use the camera, processor and communication module of a laptop computer, a personal computer or a tablet computer.

It is noted that external camera 220 may also be wore by a user (usually other than the patient, but not necessarily so). For example, a camera which is installed on glasses (such as Google-Glass™) or on another type of optical head-mounted display (OHMD, e.g. augmented reality glasses) may be used. Likewise, external camera may be installed on any other wearable device such as a watch, a garment, and so on.

External camera 220 may also be a range camera, which is operable to generate a 2D image showing the distance to points in a scene from a specific point (the location of external camera), an image which is also referred to as "range image". It is noted that both positioning image and/or the orientation image may be a range image, with or without additional visual data. That is, the range image can include a color value for each pixel in addition to the range value, but this is not necessarily so. It is noted that other types of 3D sensors, other than range camera, may also be used as external camera 220, as long as they are separate from sensor 210.

Optionally, system 200 may include a display 260 (also referred to as monitor 260) which is operable to display various types of visual information, such as any one or more of the following types of visual information: images and/or videos captured by camera 220, processed versions of such images and/or videos, positioning images, orientation images, instructions regarding the way in which system 200 should be operated by a user and/or operator thereof, a graphic user interface (GUI) which utilizes association between images and physiological measures and/or physiological measurement records, and so on.

In another example, sensor 210 may be connected to a smartphone whose components serve as units 230 and 240 (and possibly 250 as well), and an external digital camera (e.g. a dedicated camera, or that of a laptop computer or of another smartphone) may be used as camera 220. Similar implementation could use the processor and communication module of a laptop computer, a personal computer or a tablet computer.

In yet another example, system 200 may be a dedicated portable physiological examination system, which is operable to perform various physiological measurements (e.g. measuring body temperatures, taking images of body parts and recording sounds of the patient body), while an external cellular phone (or another digital camera) is used as camera 220.

It is noted that camera 220 may take an image without verifying that the image shows at least a part of portable measurement system 210. Optionally, processor 250 is operable to determine whether sensor 210 is included in a field of view of camera 220 (or was included in the field of view in an image captured by camera 220). Based on the results of the determination, processor 250 may instruct a continuation of the procedure described above, if camera 220 acquired (or is capable of acquiring) a positioning image. Based on the results of the determination, processor 250 may instruct a user of system 200 (or a user of another system, or another system) that a state of system 200 and/or of the patient should be changed, in order to enable acquisition of a satisfactory positioning image.

This may be useful, for example, if the patient also operates external camera 220 (e.g. in a position or angle which does not allow her to see a screen of the camera), or if system 200 does not include a display which shows the field of view of the camera.

It is noted that processor 250 may be operable to determine whether sensor 210 is included in the field of view of camera 220 by processing an image acquired by the camera, or in any other way (e.g. by locating a beacon or a marker included in portable measurement system 210).

Optionally, synchronization module 230 (or another component of system 200) may add metadata to one or more of: the orientation image, the physiological measurement record, and the association data. Such metadata may include for example positioning data (e.g. based on GPS measurement), time stamp, IP address of a local network, etc. Among other possible uses, such metadata may be used to prevent fraud. For example, the metadata may be used to determine that the physiological measurement was executed at the street in which the patient lives, and not abroad.

Figure 4:
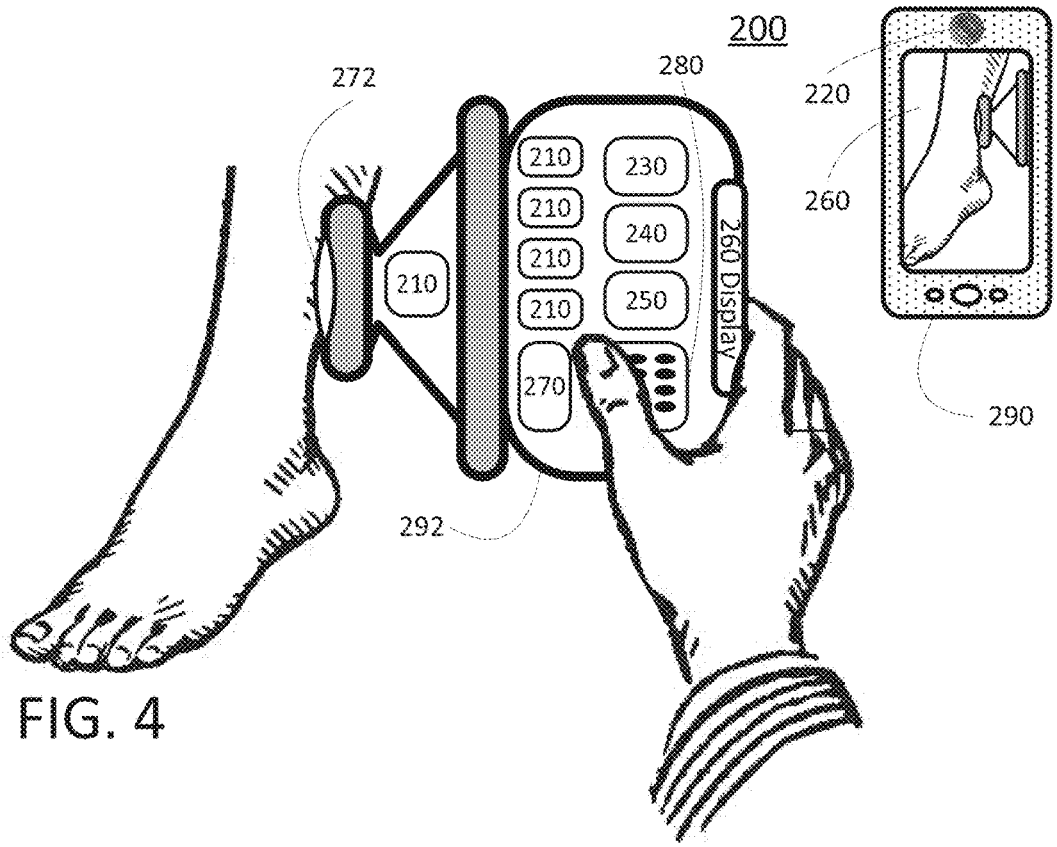

FIG. 4 is a functional block diagram illustrating an example of system 200 for measuring physiological parameters of a patient, in accordance with the presently disclosed subject matter.

As exemplified in FIG. 4, optionally sensor 210, synchronization module 230, and communication module 240 may all be part from a multi-purpose physiological examination system (denoted 292, drawn out of scale for the sake of illustration) which includes a plurality of sensors 210, such as the systems developed and produced by Tytocare LTD of Netanya, Israel. It is noted that synchronization module of system 200 may be incorporated into a processor 250 which is also capable of other processing tasks (such as a CPU of system 292). It is noted that system 292 may include a display 260 for displaying images or videos captured by the external camera, but this is not necessarily so.

While system 292 may include various sensor (such as a camera for monitoring skin, mouth, throat, eyes, and ears, temperature sensor for monitoring body temperature in various locations, microphone for auscultation (i.e. is listening or otherwise analyzing of internal sounds of the body) of the heart, lungs etc., and so on), synchronization of physiological measurements to positioning images captured by an external camera may be required for only some of the physiological measurements enabled by system 292, and not necessarily involving all of the sensors 210 of system 292. For example, visual examination of an ear of the patient (by internal imaging sensor 270 which receives light passing from lens 272) usually is not very likely to cause misinterpretation of the visual data collected by sensor 270. In comparison, analysis of auscultations and measurement of temperature may benefit from external positioning data provided by the external camera 220 (which may be included in a standalone smartphone 290 as illustrated, or any other external camera).

Optionally, synchronization module 230 is integrated with portable measurement system 210.

Reverting to FIG. 1, It is noted that the operation of camera 220 and the operation of portable measurement system 210 may be coordinated, in the sense that camera 210 should acquire the positioning image when the portable measurement system 210 is located next to the examined body location—during, just before, or just after the acquisition of the physiological measurement from the examined body location. However, it is not necessarily so. For example, in some implementations the synchronization module may simply choose a frame out of a video taken by external camera 220 based on a time tag of the physiological measurement, without actually synchronizing the operation of sensor 210 and of camera 220 in real time.

The terms "just before" or "just after" within the scope of the present disclosure do not pertain to a specific span of time, but rather to the time in which the sensor 210 is not moved from the examined body location to another location. The sensitivity of such movement depends on the type of physiological examination—while body temperature may be relatively less sensitive to exact location (e.g. displacements of 10 cm may be tolerable, in certain implementations), auscultation of the heart may tolerate much smaller displacements (e.g. 1 cm).

The coordination may be implemented by the triggering of one unit of system 200 by another unit. For example, sensor 210 may trigger (or otherwise instruct) camera 220 to acquire the positioning image when it is executing the physiological measurement. Alternatively, camera 220 may trigger execution of the physiological measurement by sensor 210 (e.g. when a person operating camera 220 determines that sensor 210 is sufficiently near a desired body location). Synchronization module 230 may also be operable to trigger operation of sensor 210 and/or of camera 230. Optionally, the triggering of the physiological measurement and/or of the capturing of the positioning image may be Optionally, synchronization module 230 may be operable to trigger the measurement of the physiological measurement by portable measurement system 210, and to control a creation of the positioning image. Synchronization module 230 may control the creation of the positioning image in different ways, such as instructing camera 220 to take an image, by instructing camera 220 to select an image out of multiple image camera 220 shots, by selecting an image out of multiple images provided by camera 220, and so on.

Optionally, the positioning image is selected from a sequence of images (either a video or another type of sequence of a plurality of still images) captured by external camera 220. The selecting of the positioning image out of the sequence of images may be executed by camera 220, by synchronization module 230, by communication module 240, or by a collaboration of two or more of these components 220, 230 and 240. It is noted that in cases external camera 220 captures a sequence of images, camera 220 may be configured to acquire a sequence of images (e.g. a video) over a span of time which is shorter than the physiological measurement. For example, if the physiological measurement takes a minute to complete, the video captured by camera 220 may be 5 seconds long.

System 200 may include a user interface 280 (UI) for receiving inputs from a user of the system, and potentially for providing information for a user of the system. User interface 280 may be a physical user interface (e.g. as illustrated in FIG. 4, including physical buttons, switches, etc.), a software user interface (e.g. an Application programming interface, API), a touchscreen user interface (e.g. using display 260), and so on.

Optionally, system 200 may include user interface 280 which is operable to transmit an interaction indication to synchronization module 230 upon identification of a human interaction (with UI 280) which satisfy at least one predetermined interaction criterion. The interaction criterion may pertain to the type of information received by the interaction with the UI, but may also pertain to other types of criteria such as time of the day, state of sensor 210, state of another component of system 200, relationship between a component of system 200 and the body of the patient (e.g. temperature measurement may requirement that a metal part of system 200 would touch the body of the patient), and so on.

Synchronization module 230 may optionally be operable to trigger the measurement of the physiological measurement by portable measurement system 210 in response to the interaction indication. For example, the user (either the patient or another person) may press a button, requesting that the physiological measurement would start. The same interaction indication may be processed in order to trigger the acquisition and/or selection of the positioning image, but this is not necessarily so.

Naturally, the user interface may be used to enable control by a person (or software) of other functionalities of system 200, such as the duration and/or operational parameters of the physiological measurement duration.

Optionally, system 200 may include a monitor (e.g. display 260) operable to display to the user positioning instructions indicating a body location for measurement. The instructions may be textual, visual, and may relate to an image acquired by the external camera 220 or by another camera of system 200 (e.g. 270). It is noted that such instructions may also be provided using a speaker, or another form of user interface.

It is noted that system 200 may be used by performing a physiological measurements in different body locations, and the plurality of positioning images (and/or orientation images) may than be used in order to determine which examined body location was examined in each physiological measurement.

Optionally, portable measurement system 210 may be operable to acquire physiological measurements from a plurality of examined body locations of the patient; the synchronization module 230 may be operable to associate to each physiological measurement out of the plurality of physiological measurements a corresponding positioning image captured by external camera 220; and communication module 240 may be operable transmit to remote system 300:
 a. physiological measurement record corresponding to each physiological measurement out of the plurality measurements,
 b. a plurality of orientation images which are based on the positioning images, and
 c. association data associating each orientation image and the corresponding physiological measurement record.

It is noted that in some situations, a single continuous physiological examination can be executed in different body locations. Such a continuous physiological examination includes measuring at least one kind of physiological parameter throughout the entire physiological examination, and may include continuous measurement and/or discreet measurements. It is noted that portable measurement system 210 does not necessarily have to touch the body throughout the entire physiological examination. The continuous physiological examination may include measuring one or more physiological parameters in discreet locations, or along a path.

Referring to the above, the continuous physiological examination may include, for example, measuring blood pressure in different body locations, measuring hardness levels of the belly along a continuous path, measuring perspiration in different locations or along a path, and so on.

Synchronization module 230 may be is operable to receive during such a continuous physiological examination (including one or more physiological measurements) multiple triggering indications, and in response to each of the multiple triggering indications to associate a positioning image to a physiological measurement measured during the continuous physiological examination. For example, if a continuous sampling of sound is collected by portable measurement system 210 from different parts of the lungs, synchronization module 230 may be triggered to associate a positioning image to different parts of the continuous sound file (e.g. by including corresponding time markers in the file, which are associated to the different images). Processor 250 and/or communication module 240 may process each of the positioning images. It is noted that the association data may be a marker in any type of prolonged measurement, and not only in sound recordings.

Optionally, system 200 may include an image processing module (e.g. part of processor 240) which is operable to process the positioning image to identify a location of the portable positioning system within the positioning image. Communication module 240 in such a case is operable to transmit to the remote system information indicative of the location of the portable positioning system within the positioning image (either as part of the orientation image, or separately from which). Some of the ways in which such identification of the sensor may be achieved and facilitated are discussed below with respect to stage 850 of method 800.

Figure 5:
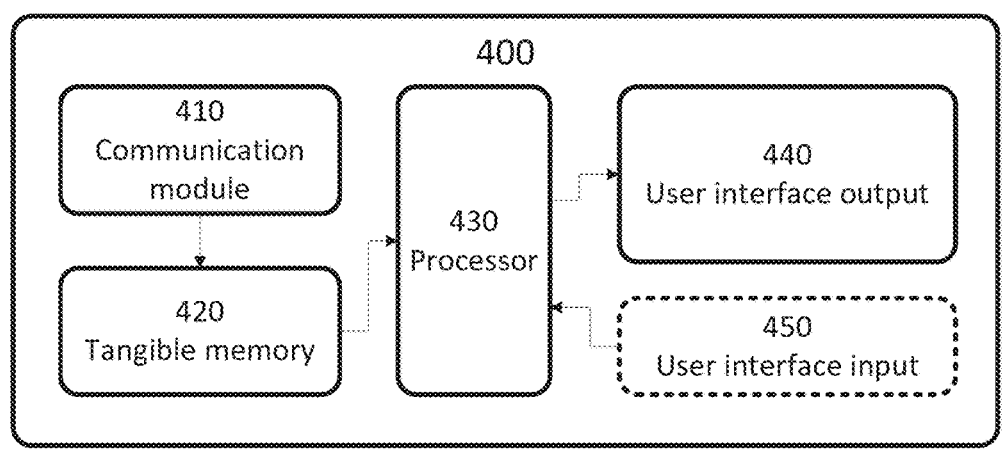
FIG. 5 illustrates a physiological monitoring system, in accordance with examples of the presently disclosed subject matter.

FIG. 5 illustrates physiological monitoring system 400, in accordance with examples of the presently disclosed subject matter. It is noted that system 400 may serve as remote system 300 to which system 200 transmits data, and may also receive information from external system 300 which acts as an intermediary system between system 200 and system 400.

System 400 includes at least communication module 410, processor 430 and user interface output 440, but may also include additional components, e.g. as discussed with respect to system 200. System 400 may also include tangible memory 420. System 400 may be a system dedicated for physical monitoring (especially designed for this purpose and not having other general computing abilities), but may also be implemented on a general purpose computer (e.g. a personal computer, a laptop computer, a smartphone, etc.), or on a computer having another use (e.g. a system which is used for managing patient information of many patients, including schedules visits, and so on).

While not necessarily so, system 400 may be operated by a trained person (e.g. a medical expert, a physician, a nurse, a physiotherapist, and so on).

Communication module 410 is operable to receive:
 a. a plurality of physiological measurement records of a plurality of physiological measurements acquired at different positions with respect to a body of a patient,
 b. a plurality of visible light orientation images (i.e. images which are based on visible light collected by an imaging sensor), each of the plurality of orientation images being indicative of a location of a portable measurement system with respect to the body of the patient, and
 c. association data associating each orientation image with a corresponding physiological measurement record out of the plurality of physiological measurement records.

It is noted that all of the terms used in the description of system 400 which were previously used in the description of system 200 (e.g. "physiological measurement record") hold the same meaning. Nevertheless, system 400 may obtain the information received by communication module 410 from system 200 other than system 200.

For the sake of example, such information may be received from the sensor and by receiving video data from a video camera which is not related to the sensor executing the physiological measurement, and detecting when the measurement is taken by processing the video—e.g. by determining when a LED light indicates that the sensor is active. Referring to such an example, it is noted that the association data (and possibly also other data received by communication module 410) may be generated by a processor of system 400. However, optionally system 400 may receive all of the aforementioned information from system 200.

Furthermore, system 400 may be used for receiving (and possibly processing) of any of the types of physiological measurements discussed with respect to system 200, such as (but not limited to) blood pressure, blood saturation, electrocardiogram (ECG) measurements, audio signals (e.g. of the heart operations or of the lungs), ultrasound signals (e.g. of the heart, of the intestines, etc.), body tissue electrical resistance, hardness of body tissues, and so on.

System 400 may include tangible memory 420 which is operable to store the plurality of physiological measurement records, the plurality of orientation images, and the association data. The term "tangible memory" is widely used in the art, and should be construed in a nonlimiting way to include memory units such as: a hard-disk drive, an optical compact disk, a random access memory (RAM), a flash drive, nonvolatile memory, or any other type of tangible memory known in the art. It is noted that tangible memory 420 may be physically connected to processor 430, but may also be located at a separate unit (e.g. on a server, an external hard-disk, on a cloud computing service, etc.), or on different such units in different locations (e.g. if cloud storage is used).

Processor 430 is operable to process the association data and to retrieve from a physiological measurements database, based on results of the processing:
  a. A selected physiological measurement record; and
  b. At least one matching orientation image.

It is noted that the physiological measurements database may be stored on one or more tangible memory units 420, as discussed above. The physiological measurement database stores a plurality of physiological measurement records and orientation images, but may also include association data and other information required for the operation of systems 400, 300 and/or 200. Optionally, processor 430 may be operable to process the association data and to retrieve from tangible memory 420, based on results of the processing, a selected physiological measurement record and at least one matching orientation image. It is noted that based on the results of the processing, processor 430 may retrieve from tangible memory 420 all of the selected physiological measurement record or only a part of that record.

User interface output 440 configured to display the at least one matching orientation image in combination with providing information of the selected physiological measurement record. The term "user interface output" pertains to the type of user information which emits information (such as a speaker, a display, and so on). Nevertheless, system 400 may also include a user interface input for receiving information from an operator of system 400.

It is noted that displaying the at least one matching orientation image in combination with providing information of the selected physiological measurement record could be implemented by displaying the at least one matching orientation image concurrently to the providing of the information of the selected physiological measurement record. However, that is not necessarily so, and the displaying in combination with the providing could also be executed in other forms of combination. For example, selecting of the displayed orientation image by a user could result in providing (e.g. displaying, playing, etc.) the information of the selected physiological measurement. The combination between the displaying and the providing requires either simultaneousness between the displaying and the providing, and/or presenting the two in a way in which the connection between the two is clear to a user of the system.

It is noted that orientation image presented by UI 440 output may be an imaged captured by external camera 220 (either processed by image-processing algorithms or not), but may also be another kind of an orientation image. For example, the orientation image displayed may be a scheme of a human body, on which a place of the examined body location (and/or a location of the sensor during measurement) is illustrated. As pointed out above, at a later stage, a textual description may replace the orientation image, so once a medical expert (or another user/software) recognized the examined body location, a description may be presented to later users, instead of the orientation image or in addition to the orientation image.

Optionally, system 400 may include a user interface input 450 for receiving information from an operator of system 400. User interface input 450 may be a physical user interface (e.g. including physical buttons, switches, etc.), a software user interface (e.g. an API), a touchscreen user interface (e.g. using a display of UI 440), and so on. Among other optional functionalities, UI input 450 may be used in order to enable a user of system 400 to review a physiological measurement of a patient and an orientation image associated with that physiological measurement. Thereby, the user can associate the physiological measurement to the examined body location near which the sensor was located. At a later stage, the user may associate the physiological measurement with a textual description, in order to speed up the orientation of the physiological measurements at other time it is reviewed.

The selection of a pair of physiological measurement and orientation image by the user via UI input 450 may be executed, for example, in one of the following ways:
  a. By the user selecting an orientation image and then being provided with the relevant one or more physiological measurements.
  b. By the user selecting a physiological measurement (e.g. an ultrasound image, or a time in a sound file of an auscultation) and then being provided with the relevant one or more orientation images.

Optionally, user interface output 440 may be configured to display a plurality of orientation images associated with different physiological measurement records, and physiological monitoring system 400 may further include a user interface input 450 for receiving a selection indication, indicative of an orientation image out of the plurality of orientation images. In such cases, processor 430 may be operable to retrieve the selected physiological measurement records based on the selection indication.

Optionally, user interface output 440 may be configured to display identifiers of a plurality of physiological measurement records, and physiological monitoring system 400 may further include user interface input 450 for receiving a selection indication, indicative of physiological measurement record out of the plurality of physiological measurement records. Processor 430 may be operable to retrieve the selected physiological measurement records based on the selection indication.

Optionally, user interface output 440 may be operable to display a video which includes the plurality of orientation images, wherein the processor is operable to retrieve from the tangible memory the physiological measurement records, and to synchronize providing information of the different physiological measurement records with the displaying of the video, based on the association data.

For example, the video may be a video of an auscultation procedure of the lungs of the patient, as captured by external camera. When processor 430 of system 400 determines that a sound sample matches a part of the video (either by association with a specific frame of the video or based on matching time tags, or in any other way), it can play the relevant sound captured by the microphone (sensor 210 in the present example) when it was placed next to the examined body part shown in the video.

Figure 6:
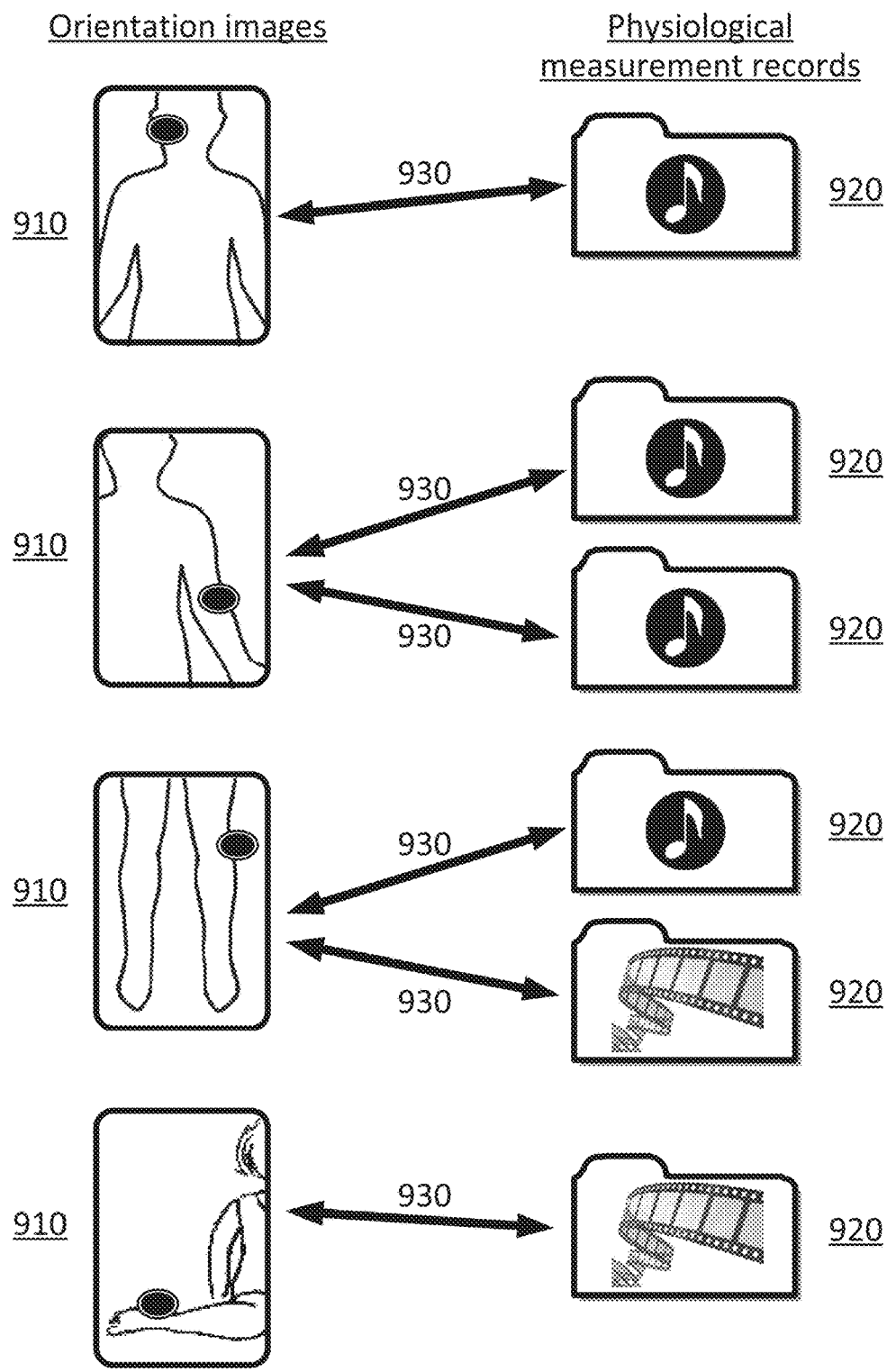
FIG. 6 illustrates an example of a database for storing association information between orientation images and physiological measurement records, in accordance with the presently disclosed subject matter.

FIG. 6 illustrates an example of a database 900 for storing association information between orientation images and physiological measurement records, in accordance with the presently disclosed subject matter. Database 900 may be stored, for example, on tangible memory 420 of system 400, but this is not necessarily so. It is noted that other types of databases may be used in system 400, instead of database 900.

Database includes three types of records. Records 910 include orientation images, or links or pointers to the orientation images, e.g. if the orientation images are stored in another database. The location of the portable measurement system which executes the measurement is represented in each of the orientation images of FIG. 6 as a black ellipse.

Records 920 include physiological measurement records, or links or pointers to the physiological measurement records, e.g. if the physiological measurement records are stored in another database. In the illustrated example, there are two types of physiological measurement records—sound samples (represented by a note) and video samples (represented by a film). However, it is clear that more (or less) types of physiological measurement records may be used, e.g. depending on the capabilities of the physiological measurement system.

Records 930 include association information between records 910 and records 930. As can be seen, optionally a single orientation image can be associated to more than one physiological measurement (of one or more types). Optionally, more than one orientation image may be associated to a single orientation image. It is noted that optionally, some of the physiological measurement records will not be associated to any orientation image (e.g. records of physiological measurement which do not require additional location information, e.g. images of the entire ear).

Figure 7:
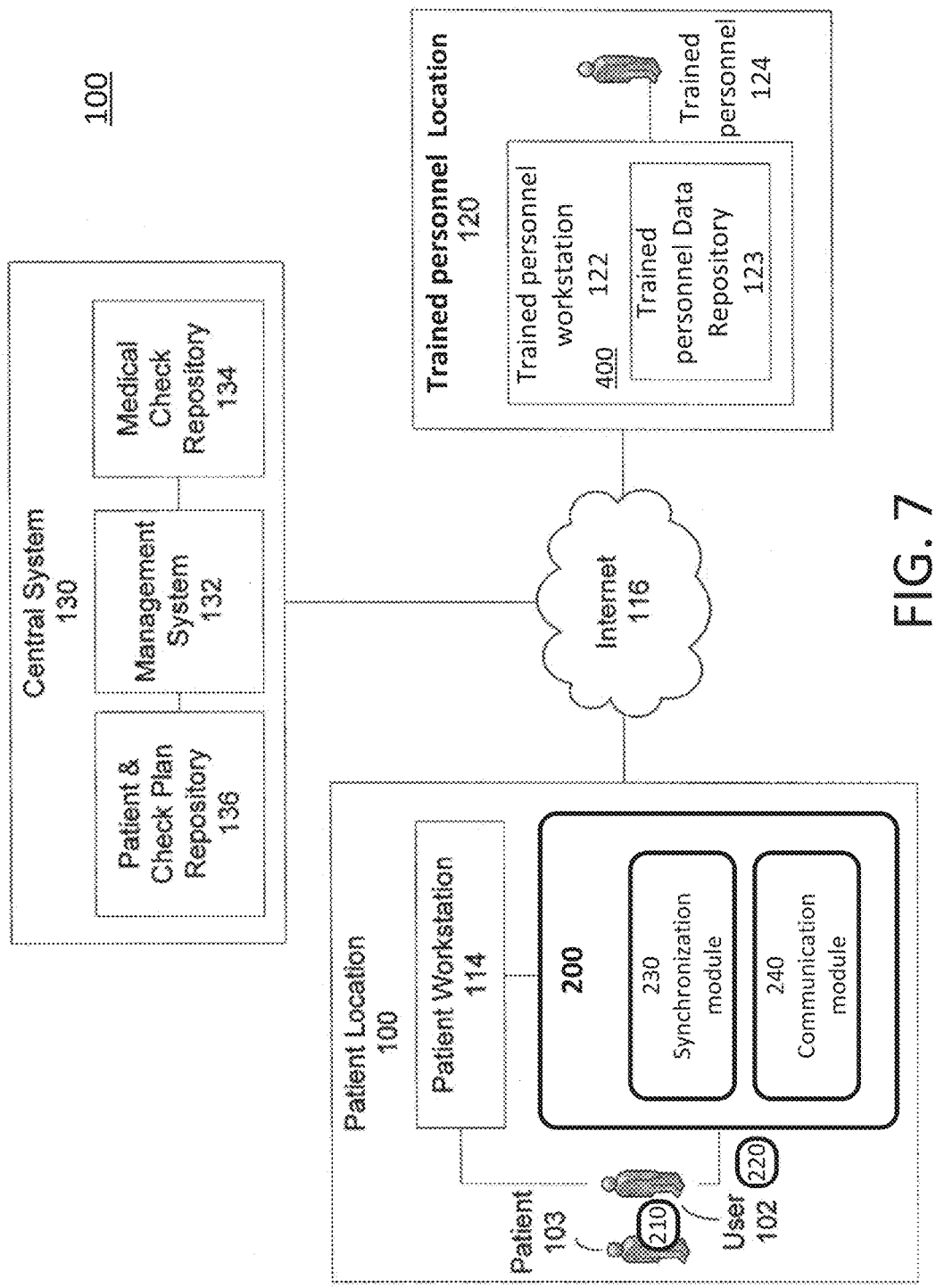
FIG. 7 is a block diagram schematically illustrating an example of an architecture of a system for performing a self-guided medical examination, in accordance with the presently disclosed subject matter.

FIG. 7 is a block diagram schematically illustrating an example of an architecture of a system 100 for performing a self-guided medical examination, in accordance with the presently disclosed subject matter. It can be appreciated that user 102 and patient 103 are located at patient location 100. User 102 can in some cases be patient 103 whose medical examination is required (in such cases, even though user 102 and patient 103 are shown as separate entities in the drawings, they are in fact the same entity). In other cases, user 102 can be a person that will be performing the medical examination of patient 103.

As illustrated in the example of FIG. 7, the systems (and likewise the methods) described in the present disclosure may be used in scenarios in which one or more trained people (denoted "trained personnel" e.g. a medical expert, a physician, a nurse, a physiotherapist, and so on) are not present next to the patient 103 at the time in which the physiological measurement. The systems and methods described in the present disclosure enable the trained personnel to learn under what conditions was the physiological measurement executed, and whether the physiological measurement was carried out according to the required procedure (either planned by the trained personnel, according to well accepted medical protocol, or in any other way).

The systems and methods described in the present disclosure also enable guidance of the patient 103 (or the user 102) during the process of physiological measurement, and in the preparations before the physiological measurement. The guidance may include guidance on how to located the portable measurement system, but may also include additional guidance (e.g. regarding to posture of the patient, on how to handle the portable measurement system, on breathing instructions, and so on).

Furthermore, the systems and methods described in the present disclosure further enable significant reduction in the chances of incorrect diagnosis, because the trained personnel can see for themselves where a physiological measurement was acquired—without having to count on the accounts of the inexperienced lay patient 103 or user 102.

For the purpose of performing a medical examination, user 102 operates system 200 as a diagnostic device, as further detailed below. In some cases, user 102 also operates an optional patient workstation 114, as further detailed below. Patient workstation 114, if implemented, can be any computer, including a personal computer, a portable computer, a cellular handset or an apparatus with appropriate processing capabilities, including a computer and/or an apparatus which can be, for example, specifically configured for that purpose. It is to be noted that in some cases, patient workstation 114 can be incorporated within system 200. System 200 may include (or is otherwise associated with) at least one processor 220 (e.g. digital signal processor (DSP), a microcontroller, a field programmable gate array (FPGA), an application specific integrated circuit (ASIC), etc.) and a memory unit 2050 (e.g. ROM, hard disk, etc.). Processor 220 may be configured to receive instructions and control the components and operations of system 200.

In some cases system 200 can be configured to communicate with patient workstation 114. The communication between system 200 and patient workstation 114 can be realized by any communication means, e.g. via wired or wireless communication. It can be noted that user 102, patient 103, system 200 and patient workstation 114 are located at patient location 100.

System 200 can be configured to acquire various types of physiological measurement data, as discussed above. The acquired data can be transmitted (directly from system 200 or through patient workstation 114) to trained personnel workstation 122 located at trained personnel location 120 and/or to an optional central system 130. Central system 130 may be operated, for example, by a medical service provider.

Central system 130 and trained personnel workstation 122 can be any computer, including a personnel computer, a portable computer, a cellular handset or an apparatus with appropriate processing capabilities, including a computer and/or an apparatus which can be, for example, specifically configured for that purpose. For example, the transmitted data (as discussed with respect to system 200 above) can be transmitted, for example, via Internet 116, or another form of computer network.

It is to be noted that the data can be transmitted while utilizing other known communication alternatives, such as a cellular network, VPN, LAN, etc. It is noted that central system 130 may be located in the same building as system 200, but this is not necessarily so, and it may even be located in another city or in another country. Likewise, trained personnel location 120 may be located in the same building as system 200 (and/or in the same building as central system 130), but this is not necessarily so, and it may even be located in another city or in another country.

Central system 130 may include patient & check plan repository 136 in which varied data relating to the patient is maintained. Such data can include, for example, patient identification number, patient name, patient age, patient contact details, patient medical data (such as diseases, sensitivities to medicines, etc.), check plans data (as further detailed below), etc. Central system 130 can further include a medical examination repository 134 in which data acquired by system 200 and patient workstation 114 is maintained. Such data can include, for example, results of medical examinations performed using diagnostics device (such as ear readings, lungs or heart recorded sound, blood pressure, body temperature, etc. as further detailed below). Central system 130 further includes management system 132 configured to forward received data to a selected trained personnel workstation 122 (for example an available trained personnel workstation 122 or trained personnel workstation 122 with the shortest queue).

It is to be noted that when providing a central system 130, there may be more than one trained personnel location 120 and trained personnel 124 as central system 130 allows for a distributed approach in which data can be received by the central system 130 from multiple patient locations and transferred by it to multiple trained personnel locations. Thus, in case the transmitted data is received at central system 130, the data is saved in medical examination repository 134 (which may then serve as tangible memory 420, in such a case) and management system 132 can transmit the received data to trained personnel location 120 (e.g. via Internet 116, or in other form of communications). In some cases, management system 132 can also manage other processes such as, subscribing patients, planning scheduling of patients to available trained personnel, etc.

It is to be noted that central system 130 is optional to the solution and that optionally central system 130 may be part of the trained personnel system 120, In addition the communication between the patient location 100 to the trained personnel location 120 can be implemented directly without the use of or need for a central system 130.

When the transmitted data is received at trained personnel workstation 122, the data can be saved in trained personnel data repository 123 (which may serve as tangible memory 420) that can be connected to trained personnel workstation 122 (which may operate as system 400). A trained personnel 124 (e.g. a doctor, a nurse, a medic, etc., including any other person with the know-how and skill to acquire and/or analyze medical data), located at trained personnel location 120, can retrieve and review the acquired data (e.g. as discussed with respect to system 400), for example using trained personnel workstation 122.

It is to be noted that patient workstation 114, trained personnel workstation 122 and central system 130 can include a display (e.g. LCD screen), and a keyboard or any other suitable input/output devices. In some cases, trained personnel 124 can provide feedback to user 102, for example by transmitting data back to patient workstation 114. Such feedback can include, for example, analysis of the received data, request to receive more data, medical treatment instructions, invitation to further examination, etc. Alternatively or additionally, trained personnel 124 can transmit feedback data to central system 130, which, in turn, can transmit the feedback data to patient workstation 114 (e.g. via the Internet, cellular network, etc.).

Referring to data transmission in the systems discussed in FIGS. 1-7, and in communication between those systems—it is noted that any transmission and/or communication of data between any two units, modules, systems, processors etc. of any one of the systems discussed above may be executed in a wired manner, in a wireless manner, or as a combination of both. For example, some of these units, modules, systems, processors etc. may be connected using USB communication, over a serial bus, using LAN network, over the Internet, over hybrid fibre-coaxial (HFC) network, and so on. For example, some of these units, modules, systems, processors etc. may communicate wirelessly, e.g. over cellular telephony, Wi-Fi, Bluetooth, satellite communication, and so forth. For example, any one of the following communication channels discussed above (explicitly or implicitly) may use wired, wireless or combined communication:

a. Communication between any two (or more) of: portable measurement system 210, external camera 220, synchronization module 230, the communication module 240, and processor 250.
b. Communication between any two (or more) of: communication module 410, memory unit 420, processor 430, UI 440, UI 450.
c. Communication between any two (or more) of: system 200, system 300, and system 400.

Figure 8:
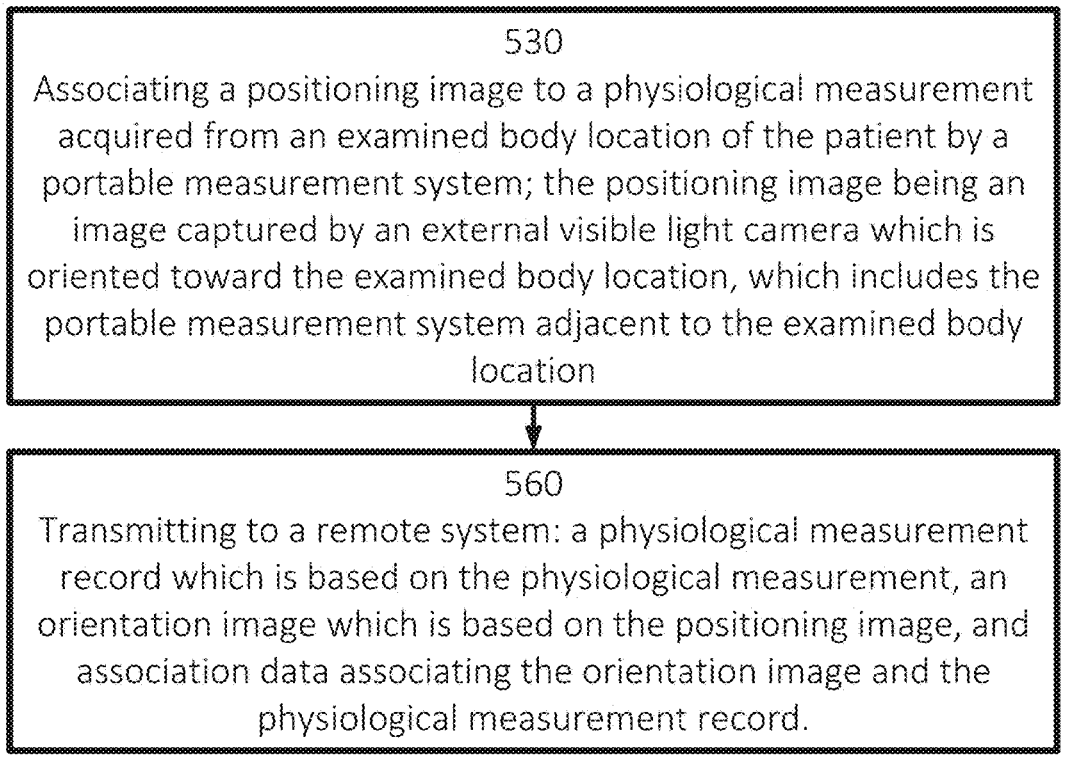
FIGS. 8, 9, and 10 are flow charts illustrating examples of methods for measuring physiological parameters of a patient, in accordance with the presently disclosed subject matter.

FIG. 8 is a flow chart illustrating an example of method 500 for measuring physiological parameters of a patient, in accordance with the presently disclosed subject matter. Referring to the examples set forth with respect to the previous drawings, method 500 may be executed by system 200. It is noted that any optional variations, functionalities or structures discussed with respect to system 200 or to any one of its components could also be applied, mutatis mutandis, to method 500 or to the one or more relevant stages thereof. Method 500 includes at least stages 530 and 560.

Stage 530 includes associating a positioning image to a physiological measurement acquired from an examined body location of the patient by a portable measurement system; the positioning image being an image captured by an external visible light camera which is oriented toward the examined body location, which includes the portable measurement system adjacent to the examined body location. The external visible light camera is a camera which is not connected to the portable measurement system and which is operable to capture visible light and to generate images based on the captured light. The external camera may also be sensitive to infrared radiation (e.g. near IR), but this is not necessarily so. Referring to the examples set forth with respect to the previous drawings, stage 530 may be executed by synchronization module 230.

Optionally, the physiological measurement includes sounds of at least one lung of the patient. Optionally, the physiological measurement which is indicative of at least one blood flow parameter. Other non-limiting examples of physiological measurements were provided above with respect to system 200.

Stage 560 includes transmitting to a remote system: a physiological measurement record which is based on the physiological measurement, an orientation image which is based on the positioning image, and association data associating the orientation image and the physiological measurement record. The orientation image also includes the portable measurement system (i.e. at least part of it) adjacent to the examined body location. Referring to the examples set forth with respect to the previous drawings, stage 560 may be executed by communication module 240.

It is noted that the transmission of stage 560 may include transmitting of additional information, based on data of the portable measurement system and/or on data of the external camera. For example, such additional data may include—time labels; measurement parameters used by the sensor; operational parameters used by the sensor; filters used by the sensor; measurement parameters used by the external camera; operational parameters used by the external camera; filters used by the external camera; additional physiological data (e.g. heartrate of the patient at the time of measurement), and so on.

Figure 9:
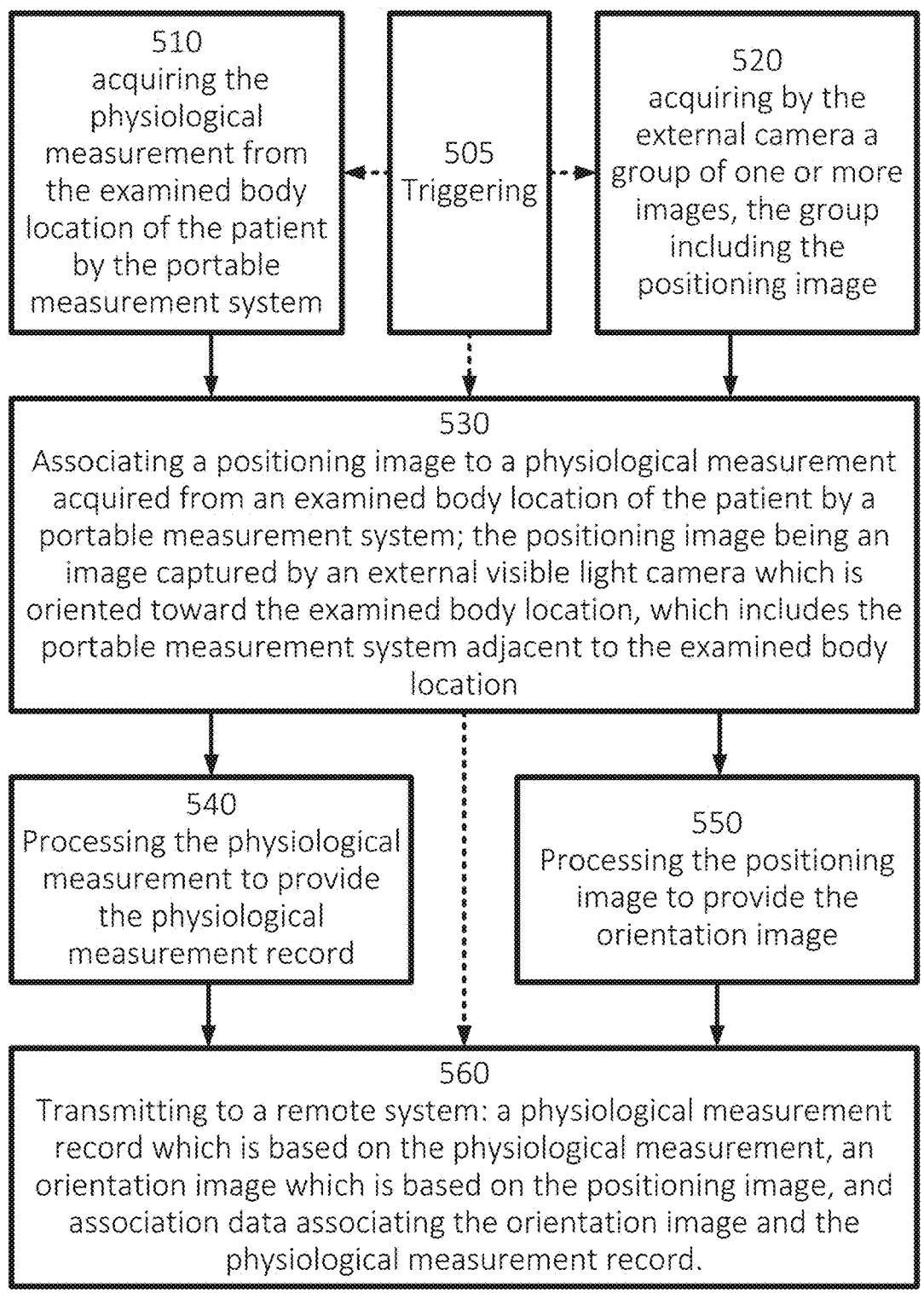

FIG. 9 is a flow chart illustrating an example of method 500 for measuring physiological parameters of a patient, in accordance with the presently disclosed subject matter.

Optionally, method 500 may include stage 510 of acquiring the physiological measurement from the examined body location of the patient by the portable measurement system.

Referring to the examples set forth with respect to the previous drawings, stage 510 may be executed by portable measurement system 210.

Optionally, method 500 may include stage 520 of acquiring by the external camera a group of one or more images, the group including the positioning image. Referring to the examples set forth with respect to the previous drawings, stage 520 may be executed by external camera 220.

Method 500 may also include stage 505 of triggering one or more of stages 510, 520 and 530 (which may be based on a receiving a triggering indication and/or an interaction indication), and possibly of the acquisition of the positioning image (or images). It is noted that if two or more of these stages are triggered, the triggering may be in response to a single triggering event, or to multiple triggering events. For example, the physiological measurement may be initiated in response to a sensor indication that the portable measurement system touches a skin of the patient, and the association of the image may be triggered based on an indication that the physiological measurement concluded successfully.

Optionally, method 500 may include stage 540 of processing the physiological measurement to provide the physiological measurement record. It is noted that the processing of stage 540 may be based on additional data, in addition to the physiological measurement (e.g. it may further be based on operational parameters of the portable measurement system, on medical information of the patient, and so on). Referring to the examples set forth with respect to the previous drawings, stage 540 may be executed by processor 250.

It is noted that method 500 may also include processing the positioning image to identify a location of the portable positioning system within the positioning image. Several ways in which such identification can be achieved and facilitated are discussed in greater detail with respect to stage 850 of method 500. If method 500 includes such processing of the positioning image, the transmitting of stage 560 may further include transmitting to the remote system information indicative of the location of the portable positioning system within the positioning image. The additional information may be part of the orientation image (e.g. a graphical representation of the determined location of the sensor), but may also be provided separated from it (e.g. in a separate file).

Optionally, method 500 may include stage 550 of processing the positioning image to provide the orientation image. It is noted that the processing of stage 550 may be based on additional data, in addition to the physiological measurement (e.g. it may further be based on additional images acquired by the external camera, on operational parameters of the portable measurement system, on medical information of the patient, and so on). Referring to the examples set forth with respect to the previous drawings, stage 550 may be executed by processor 250. The processing of stage 550 may include, in few non-limiting examples, any one of the following: improving image quality, adding additional information (e.g. text and informative data), cropping, anonymizing, and so on.

It is noted that method 500 may also include processing the positioning image to identify a location of the portable positioning system within the positioning image. Several ways in which such identification can be achieved and facilitated are discussed in greater detail with respect to stage 550 of method 500. If method 500 includes such processing of the positioning image, the transmitting of stage 560 may further include transmitting to the remote system information indicative of the location of the portable positioning system within the positioning image. The additional information may be part of the orientation image (e.g. a graphical representation of the determined location of the sensor), but may also be provided separated from it (e.g. in a separate file).

Optionally, method 500 may include stage 550 of processing the positioning image to provide the orientation image. It is noted that the processing of stage 550 may be based on additional data, in addition to the physiological measurement (e.g. it may further be based on additional images acquired by the external camera, on operational parameters of the portable measurement system, on medical information of the patient, and so on). Referring to the examples set forth with respect to the previous drawings, stage 550 may be executed by processor 250.

Method 500 may also include additional stages. For example, method 500 may include a stage of selectively triggering the measurement of the physiological measurement by the portable measurement system in response to a user input which satisfy at least one predetermined interaction criterion.

Optionally, method 500 may include a stage of providing, via a user interface, positioning instructions indicating a body location for measurement.

Optionally, method 500 may include a stage of selecting the positioning image out of a sequence of images captured by the external camera, the sequence including a plurality of images.

Method 500 may include managing physiological measurement taken from a plurality of body locations, and the respective positioning images taken. For example, method 500 may include: acquiring physiological measurements from a plurality of examined body locations of the patient; associating to each physiological measurement out of the plurality of physiological measurements a corresponding positioning image captured by the external camera; and transmitting to the remote system: (a) physiological measurement record corresponding to each physiological measurement out of the plurality measurements, (b) a plurality of orientation images which are based on the positioning images, and (c) association data associating each orientation image and the corresponding physiological measurement record.

Referring to stage 505, it is noted that method 500 may include receiving multiple triggering indications during a continuous physiological examination, and in response to each of the multiple triggering indications to associate in stage 530 a positioning image to a physiological measurement measured during the continuous physiological examination. Stages 550 and/or 560 may be executed for one or more of these multiple positioning images.

Figure 10:
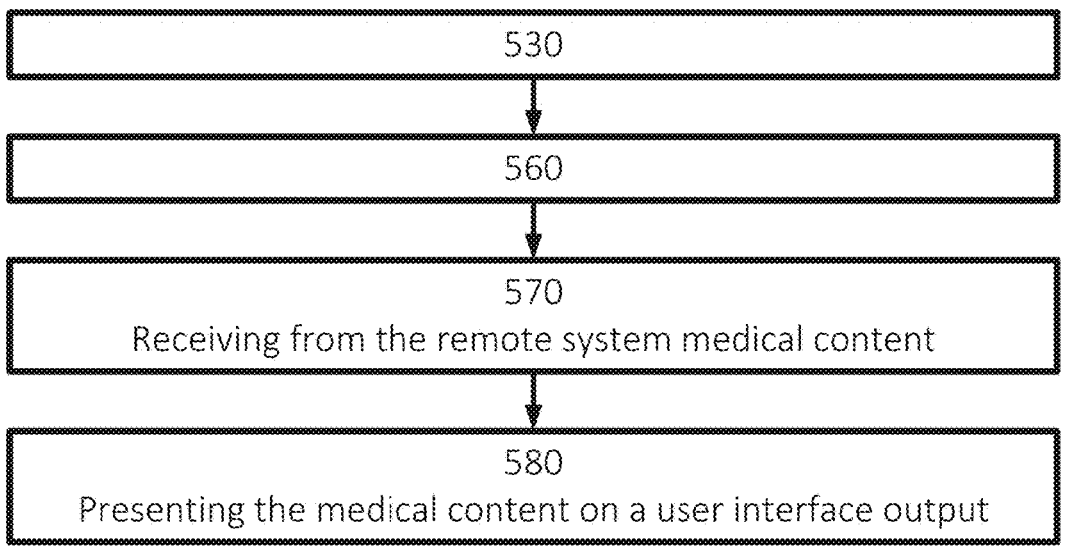

FIG. 10 is a flow chart illustrating an example of method 500 for measuring physiological parameters of a patient, in accordance with the presently disclosed subject matter.

Stage 560 may be followed by stage 570 of receiving from the remote system (or from another remote system) medical content. The medical content may include, for example, any one or more of the following: a diagnosis of a medical condition of the patient, instructions for medication to be taken by the patient, indication of further physiological measurements which are required by the patient (either using the same system, or by going to a medical center, etc.), instructions for medical treatment, and so on. Referring to the examples set forth with respect to the previous drawings, stage 570 may be executed by communication system 240. It is noted that any one or more of stages 510, 520, 540 and 550 may also be executed prior to stage 570.

Stage 570 may be followed by stage 580 of presenting the medical content on a user interface output. Referring to the examples set forth with respect to the previous drawings, stage 580 may be executed by display 260, or by another UI such as a speaker.

Figure 11:
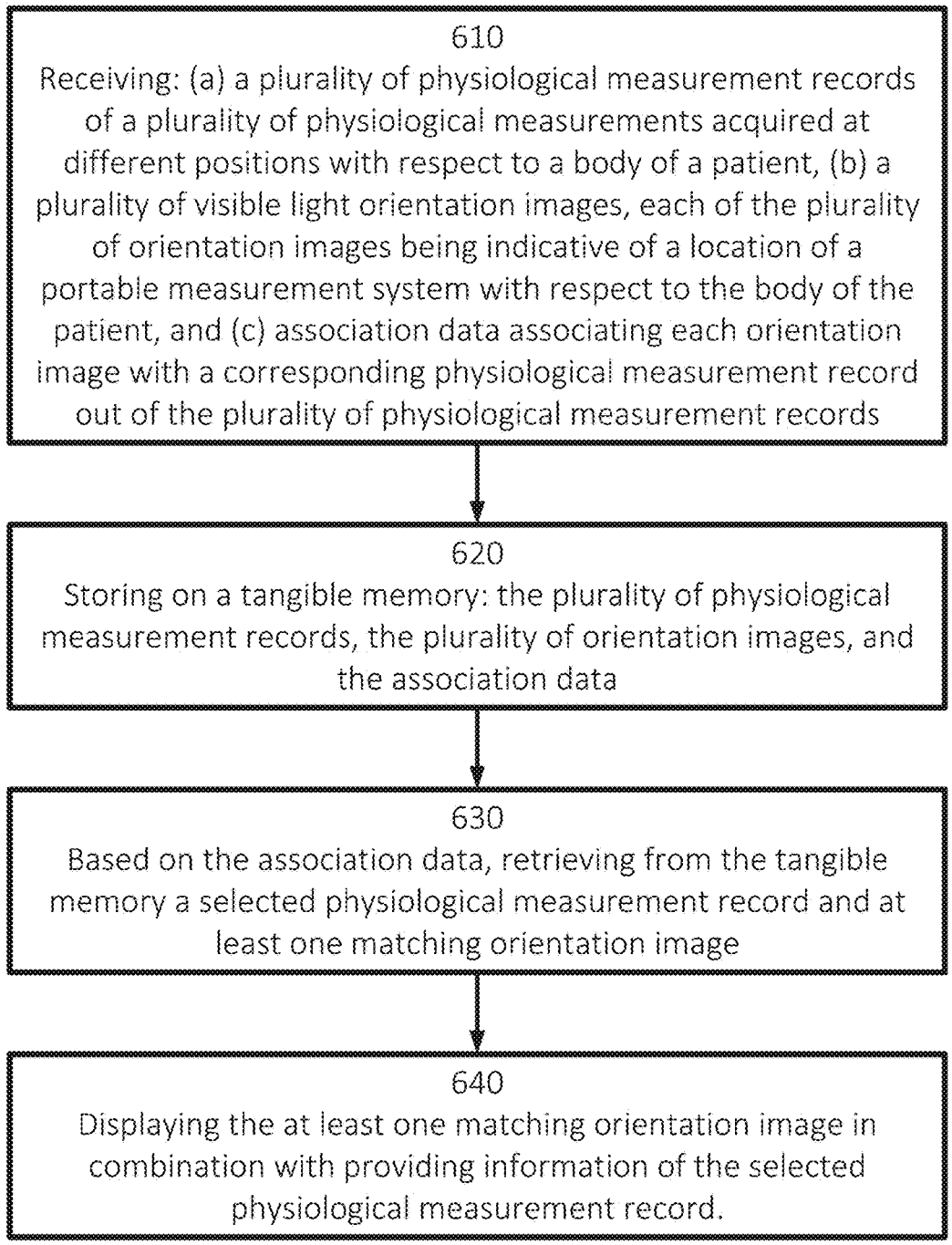
FIG. 11 is a flow chart illustrating an example of a computer-implemented method for physiological monitoring, in accordance with the presently disclosed subject matter.

FIG. 11 is a flow chart illustrating an example of method 600 which is a computer-implemented method for physiological monitoring, in accordance with the presently disclosed subject matter. Referring to the examples set forth with respect to the previous drawings, method 600 may be executed by system 400. It is noted that any optional variations, functionalities or structures discussed with respect to system 400 or to any one of its components could also be applied, mutatis mutandis, to method 600 or to the one or more relevant stages thereof.

Method 600 starts with stage 610 of receiving:
 a. a plurality of physiological measurement records of a plurality of physiological measurements acquired at different positions with respect to a body of a patient,
 b. a plurality of visible light orientation images (i.e. images which are based on visible light collected by an imaging sensor), each of the plurality of orientation images being indicative of a location of a portable measurement system with respect to the body of the patient, and
 c. association data associating each orientation image with a corresponding physiological measurement record out of the plurality of physiological measurement records.

Referring to the examples set forth with respect to the previous drawings, stage 610 may be executed by communication module 410.

Stage 610 is followed by stage 620 of storing on a tangible memory: the plurality of physiological measurement records, the plurality of orientation images, and the association data. Referring to the examples set forth with respect to the previous drawings, the tangible memory of stage 620 may be tangible memory 420.

Stage 620 is followed by stage 630 which includes retrieving from the tangible memory, based on the association data, a selected physiological measurement record and at least one matching orientation image. The retrieving may include retrieving all or part of the selection physiological measurement record. Referring to the examples set forth with respect to the previous drawings, stage 630 may be executed by processor 430.

Stage 640 of method 600 includes displaying the at least one matching orientation image in combination with providing information of the selected physiological measurement record. Referring to the examples set forth with respect to the previous drawings, stage 640 may be executed by UI output 440.

Optionally, stage 630 may be preceded by displaying a plurality of orientation images associated with different physiological measurement records (e.g. using the UI output of stage 640) and by receiving a selection indication indicative of a selection by a user of at least one out of the plurality of orientation images. Stage 630 in such a case may include retrieving the selected physiological measurement records based on the selection indication.

Optionally, stage 630 may be preceded by displaying identifiers of a plurality of physiological measurement records (e.g. using the UI output of stage 640) and by receiving a selection indication indicative of selection by a user of a physiological measurement record out of the plurality of physiological measurement records. Stage 630 may include in such a case retrieving the selected physiological measurement records based on the selection indication.

Optionally, method 600 may include displaying a video which includes the plurality of orientation images, retrieving from the tangible memory the physiological measurement records, and synchronizing providing information of the different physiological measurement records with the displaying of the video, based on the association data.

It is noted that method 600 may be implemented on a non-transitory computer-readable medium. A non-transitory computer-readable medium for physiological monitoring is disclosed, including instructions stored thereon, that when executed on a processor, perform the steps of:
 a. obtaining: (a) a plurality of physiological measurement records of a plurality of physiological measurements acquired at different positions with respect to a body of a patient, (b) a plurality of orientation images, each of the plurality of orientation images being indicative of a location of a portable measurement system with respect to the body of the patient, and (c) association data associating each orientation image with a corresponding physiological measurement record out of the plurality of physiological measurement records;
 b. storing on a tangible memory: the plurality of physiological measurement records, the plurality of orientation images, and the association data;
 c. based on the association data, retrieving from the tangible memory a selected physiological measurement record and at least one matching orientation image; and
 d. displaying the at least one matching orientation image in combination with providing information of the selected physiological measurement record.

It is noted that all other stages of method 600 may also be implemented as instructions stored on the aforementioned non-transitory computer-readable medium.

A program is disclosed, which makes a computer execute:
 a. obtaining: (a) a plurality of physiological measurement records of a plurality of physiological measurements acquired at different positions with respect to a body of a patient, (b) a plurality of orientation images, each of the plurality of orientation images being indicative of a location of a portable measurement system with respect to the body of the patient, and (c) association data associating each orientation image with a corresponding physiological measurement record out of the plurality of physiological measurement records;
 b. storing on a tangible memory: the plurality of physiological measurement records, the plurality of orientation images, and the association data;
 c. based on the association data, retrieving from the tangible memory a selected physiological measurement record and at least one matching orientation image; and
 d. displaying the at least one matching orientation image in combination with providing information of the selected physiological measurement record.

It is noted that all other stages of method 600 may also be implemented as instructions of the program, making the computer perform these stages.

Figure 12:
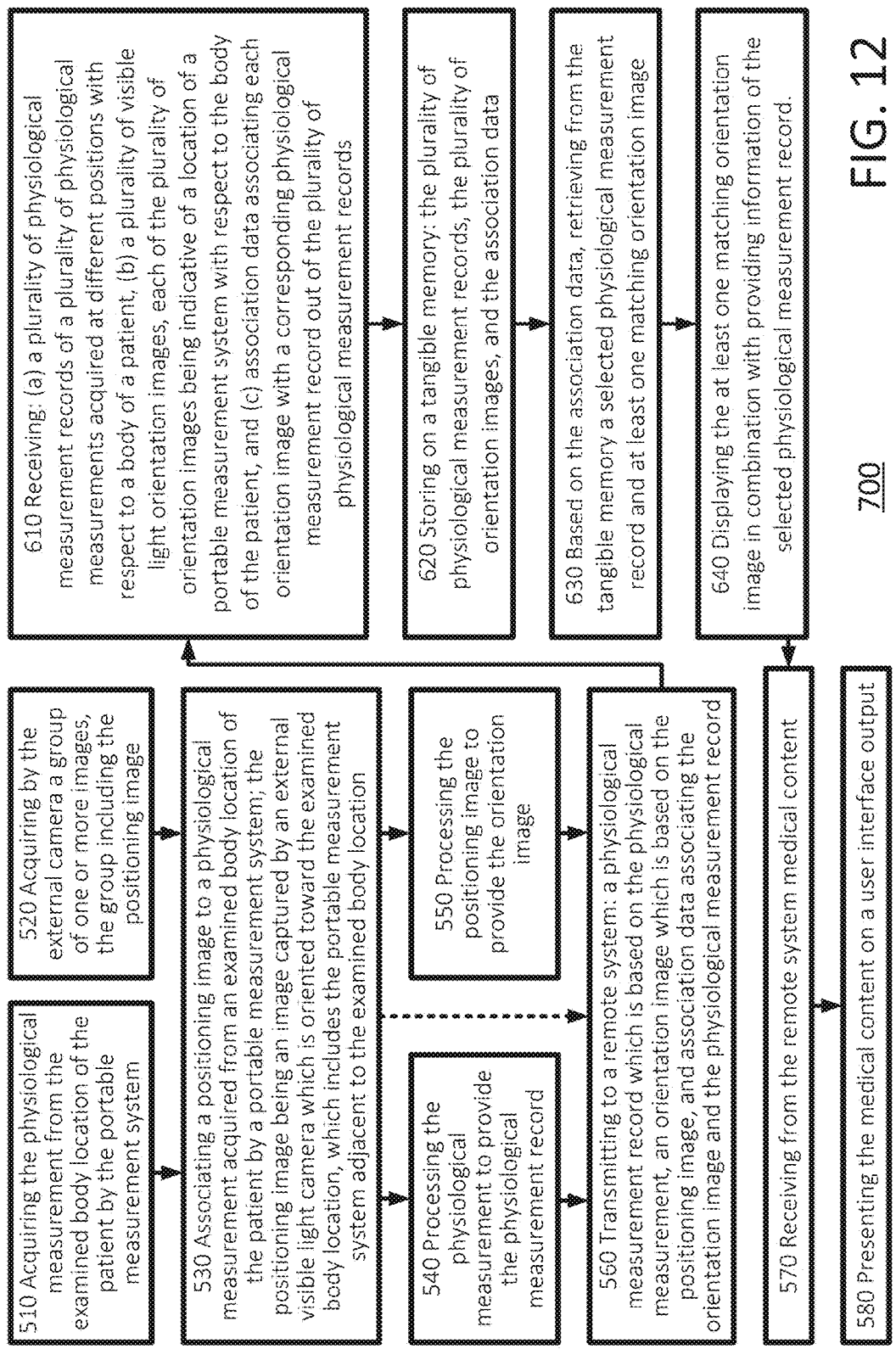
FIG. 12 is a flow chart illustrating an example of a method for physiological monitoring, in accordance with the presently disclosed subject matter.

FIG. 12 is a flow chart illustrating an example of method 700 for physiological monitoring, in accordance with the presently disclosed subject matter. Referring to the examples set forth with respect to the previous drawings, the execution of method 700 may be coordinated by system 200 and system 400. It is noted that method 700 includes at least stage 530, 560, 610, 620, 630 and 640, and may also include any combination of one or more of stage 510, 520, 540, 550, 570 and 580. Method 700 may be executed in system 100, which is discussed above with respect to FIG. 7.

FIGS. 13A and 13B are flow charts illustrating examples of anonymization in methods 500 and 600, in accordance with the presently disclosed subject matter. FIG. 13A demonstrates how anonymization could be integrated into method 500, and FIG. 13B demonstrates how anonymization could be integrated into method 600.

Referring to FIG. 13A, it is noted that stage 550 may include stage 551 of anonymizing the orientation image for removing identifiable visual information from the orientation image. It is noted that different levels of anonymization may be implemented. The level of anonymization may depend on different considerations such as: preferences of the user, regulation, business model, type of medical examination executed, intended recipient (medical, nurse, general physician, specialist, etc.), and so on. The anonymization is intended to prevent (or reduce the likelihood) of associating the orientation image to the specific individual, when it is not necessary for medical reasons.

Few non-exhausting examples for image processing algorithms which may be used for anonymization of the orientation image (or of portions of it) are:
 a. Transform-domain operations, such as: AC pseudo-random coefficients; AC sub-bands pseudo-random coefficient flipping; coefficient flipping; coefficient permutation; and subband-adaptive scrambling.
 b. Pixel-level operations, such as: blurring; pixelization; masking; k-same (and its variants, such as k-same-select; k-same-m); abstraction operators; mask faces; pixel relocation; chaos cryptography; warping.
 c. Silhouetting;
 d. Any combination of the above.

Stages 552 and 553 are examples of variations of the anonymization of stage 551. Stage 552 includes anonymizing a selected body area of the patient (e.g. the face, chest, etc.) at a higher anonymization level than other body areas shown in the orientation image. The other parts may be left not anonymized at all, or partly anonymized.

Stage 553 includes anonymizing parts of the orientation image which are far from the portable measurement system, while keeping the area around the portable measurement system coherent. This way, the person viewing the orientation image (or a system analyzing it) can have clear understanding of the positioning of the sensor, of its orientation, and so on.

If a range camera (or other 3D sensor) is used as the external camera, the anonymizing of stage 551 may also include anonymizing the background of the scene, but leaving parts of the patient coherent.

Method 500 may also include presenting an anonymized image to the user on a UI. The anonymized image may be an anonymized version of the positioning image, of the orientation image, or of another image which is based on data acquired by the external camera. Being presented with an anonymized image of herself (e.g. cartoonized, blurred, etc.), the patient may be more comfortable with the imaging process, and with the transmission of herself to a remote system. This is even more notable with medical examination which pertain exposing body parts which are not usually exposed, or when having medical conditions which people may be ashamed with.

Referring to FIG. 13B, the anonymization in this case not executed by the user-side system (as is the case in the example of FIG. 13A), but after the orientation images are sent (e.g. by a server, or by a physician system). Method 600 in such a case includes stage 650 of anonymizing one or more of the orientation images. It is noted that any of the anonymization variants discussed with respect to FIG. 13A may also be implemented as part of method 600. It is also noted that the anonymization may be executed in different stages of the method (as demonstrated by the plurality of flow arrows in the diagram): before saving the orientation image to the memory module, after saving but before selecting, or after selecting which images are to be displayed.

Stage 640 includes in such a case stage 641 of displaying an anonymized version of the at least one matching orientation image, in combination with providing information of the selected physiological measurement record.

Figure 14A:
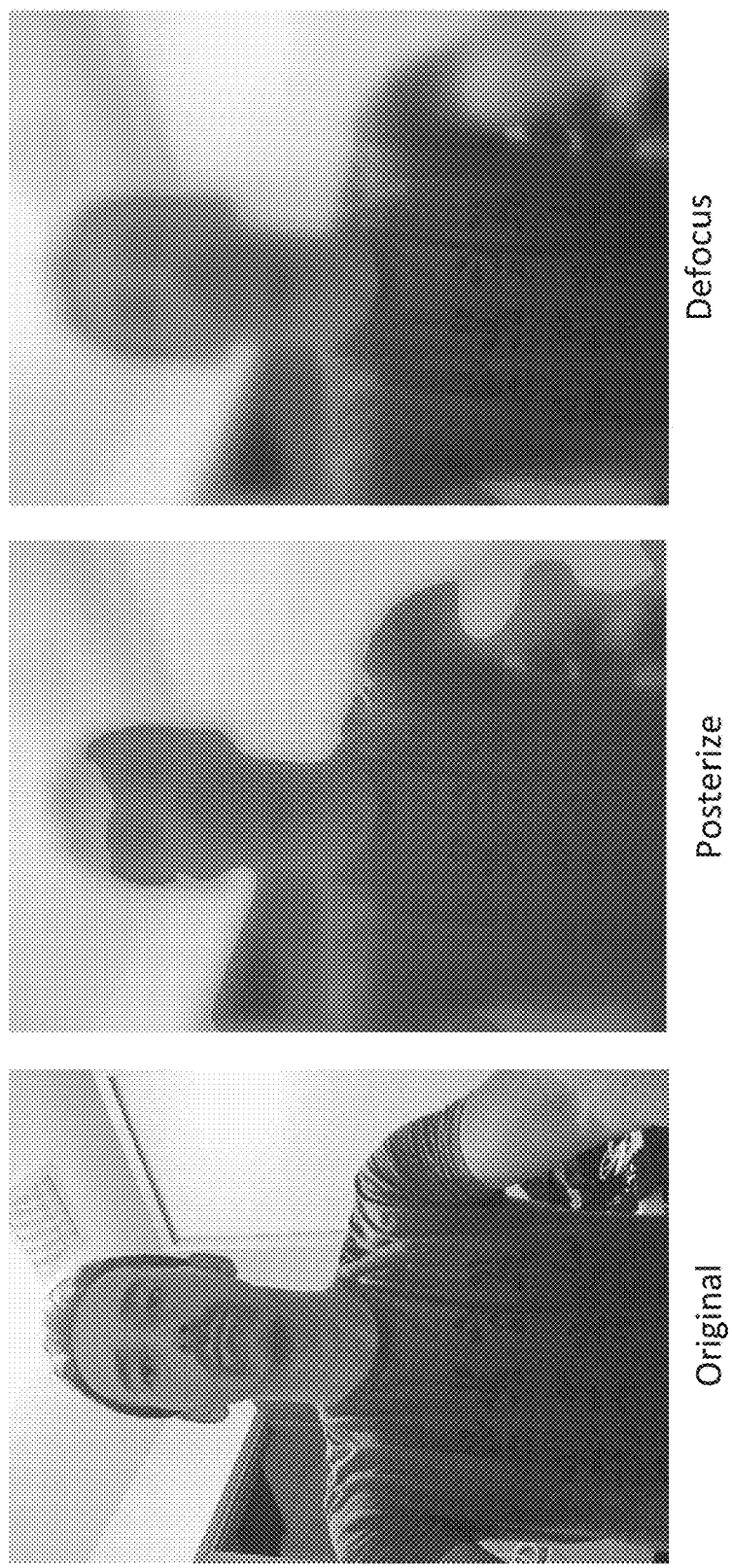
FIGS. 14A and 14B provide few examples of anonymization options in orientation images, in accordance with the presently disclosed subject matter.
Figure 14B:
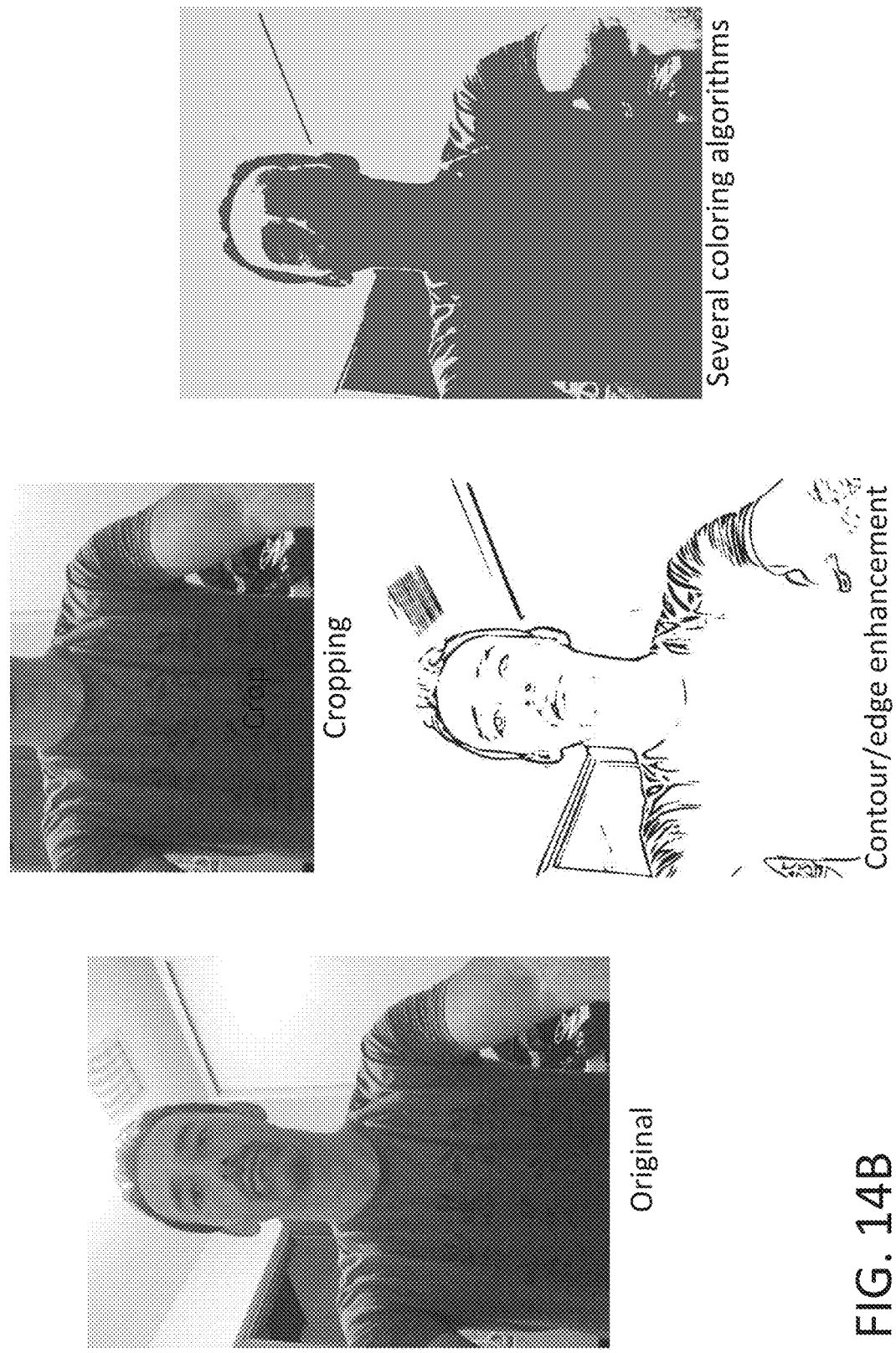

FIGS. 14A and 14B provide few examples of anonymization options in orientation images, in accordance with the presently disclosed subject matter. In each of FIGS. 14A and 14B there is an original image (denoted "original image), which can be either the positioning image, a processed version of the positioning image, or any other image acquired by the external camera (because anonymization may also be implemented in other images acquired by the external camera, such as the reference image of method 800, or a video documenting a physiological examination procedure). In addition, each of those two figures illustrate an anonymized version of the original image, to which one or more image processing algorithm have been applied.

FIG. 14A demonstrates posterizing (including conversion of a continuous gradation of tone to several regions of fewer tones) and defocusing of the original image. FIG. 14B demonstrates cropping (removing of easily identifiable parts of the image, like the face area), contour (or edge) enhancement (also referred to as "wire framing"), and the product of few image processing colored-based algorithms, applied one on the result of the other. It is clear to a person who is of skill in the art that other image processing techniques may also be used.

Figure 15:
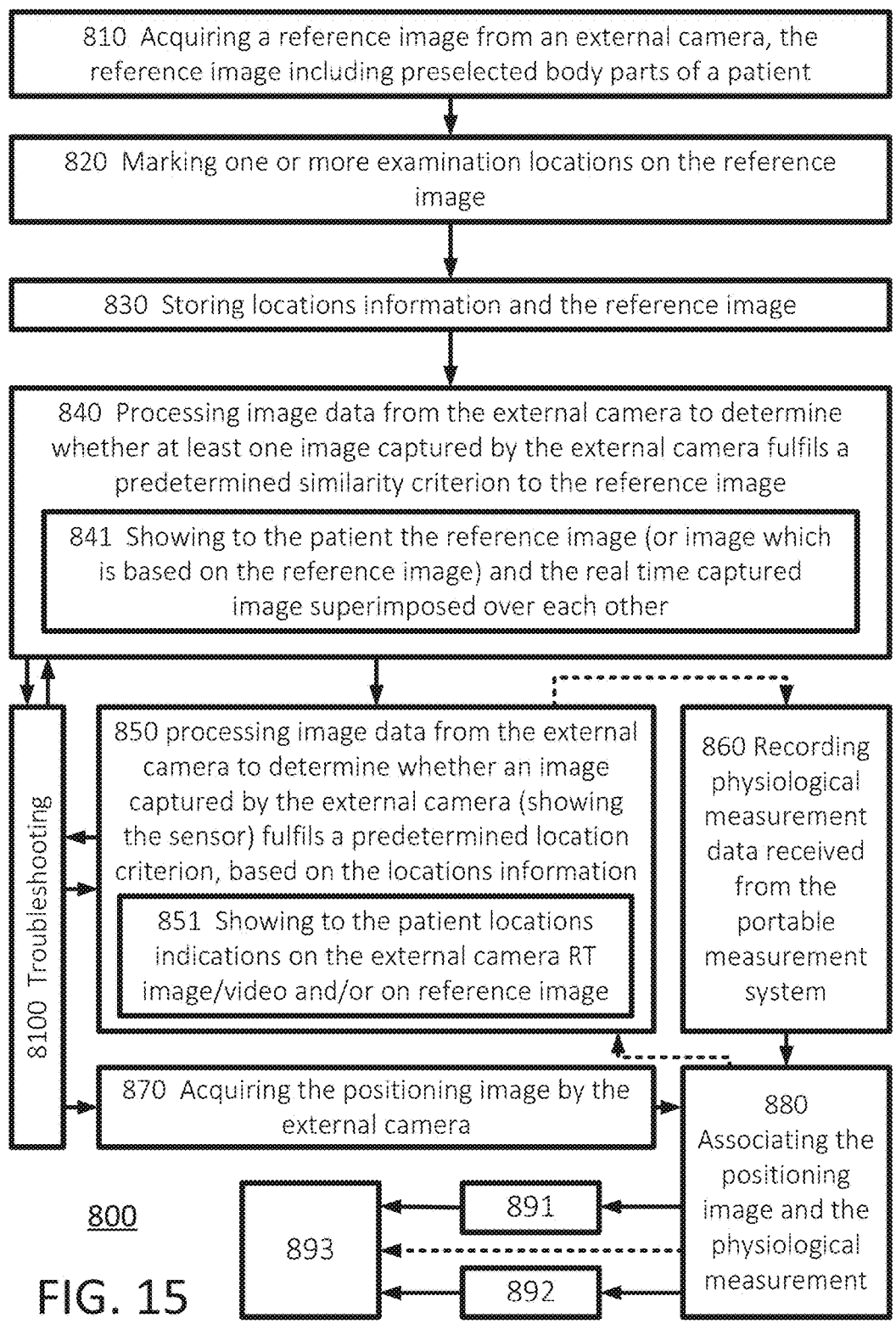
FIG. 15 is a flow chart illustrating an example of a method for physiological monitoring using a portable measurement system and an external camera, in accordance with the presently disclosed subject matter.

FIG. 15 is a flow chart illustrating an example of method 800 for physiological monitoring using a portable measurement system and an external camera, in accordance with the presently disclosed subject matter. Referring to the examples set forth with respect to the previous drawings, method 800 may be executed using system 200, system 400, or a combination thereof. Referring to the examples set forth with respect to the previous drawings, method 800 may be executed using system 1900, system 400, or a combination thereof.

Method 800 enables personalization of the examination procedures of method 500 and of system 200. This way, the examination locations—and other examination parameters (such as orientation of the portable measurement system, its pressure level against the body of the patient, and so on).

Stage 810 includes acquiring a reference image from an external camera, the reference image including preselected body parts of a patient. For example, the preselected body parts may include the face and the thorax, the face and the torso, the back and the arms, and so on. Optionally, some of the preselected body parts may be parts which are more easily identified by an automated algorithm. This way, the reference image may serve as a reference image for acquiring the positioning images of system 200 and method 500—by identifying one or more of the predefined body parts.

The preselected body parts may be selected by a medical expert or another trained personnel (and/or by the patient or another user) for the specific patient and/or for the specific examination (or other physiological measurement).

It is noted that stage 810 may be executed completely automatically or with an aid of a technician (e.g. operating a remote system on a control center). Stage 810 may include giving instructions to the user as to the positioning of herself and/or the external camera, as to posture, etc. The triggering of the acquisition of the reference image may be done by the user, by a technician (or another operator, whether on site or remote), or by an automatic algorithm which determined whether specific conditions are fulfilled (e.g. showing the preselected body parts, sufficient illumination, and so on).

Stage 820 includes marking one or more examination locations on the reference image. The marking may be done by a physician, a nurse, a technician, or another medical expert or a trained personnel. This may serve to instruct the user to bring the portable measurement system to a physiological significant location in which meaningful results can be measured. The marking may also be done by the user (or another operator in his vicinity), e.g. in order to inform the medical expert where the patient feels pain etc. It is noted that the marking may optionally be repeated or amended from time to time (e.g. based on changing medical needs of the patient, as assessed by a physician). It is noted that each examination location may be a point, and may also be a larger region of interest. Optionally, stage 820 may also include selecting other parameters for the examination, such as orientation of the portable measurement system, its pressure level against the body of the patient, and so on.

Optional stage 830 includes storing on intangible memory the reference image and locations information (which enable to verify—using image data from the external camera—whether the portable measurement system is at any selected location out of the examination locations). The storying may include storing the locations information as part of the image (e.g. as pixels metadata), or a separate data file. If additional parameters are selected in stage 820 (e.g. orientation, etc.), these parameters are also recorded in stage 830.

The following stage of method 800, starting with stage 840, are examination stages, and are intended to acquire physiological measurements from the patient, e.g. as described in method 500.

Stage 840 includes processing image data from the external camera to determine whether at least one image captured by the external camera fulfils a predetermined similarity criterion to the reference image. The image captured by the external camera is real-time image (or near real time). Stage 840 may include instructing the patient to take the position and posture for going back to the same recognizable posture of the reference image.

This way, it is possible to verify that the patient is at similar place/posture to the place/posture he was when the reference image was captured. Since the marking of the examination locations took place over the reference image—having the patient at a similar place/posture enables to adapt the examination locations to the patient at the time of examination (determining where the portable measurement system should be located with respect to the body of the patient in real time). It is noted that maintaining the same posture may be important for several types of physiological measurements.

The similarity criterion of stage 840 may be based, for example, on distances between identifiable body locations, on degree of overlap between the silhouettes of the patient in both images, on relationship between specific anchor points on the silhouette, and so on and so forth.

Stage 840 may include stage 841 of showing to the patient the reference image (or image which is based on the reference image) and the real time captured image superimposed over each other. This way, the patient can have a clear visible instruction on how to return to a similar place/posture. The image shown to the patient may be an anonymized image, as discussed with respect to FIGS. 13A and 13B. For example, the client may be required to fit into a silhouette of herself, or into a soften image of herself.

When the condition of stage 840 is fulfilled, method 800 continues to stage 850. Alternatively (or in a combined manner), method 500 may follow stage 840. It will be clear to the reader that if method 500 is combined with any part of method 800, than the external camera is the same external camera (and the data captured by it includes the positioning image), that the portable measurement system is the same portable measurement system and that the patient is the same patient.

Stage 850 includes processing image data from the external camera to determine whether at least one image captured by the external camera (in which the portable measurement system is shown) fulfils a predetermined location criterion, based on the locations information stored in stage 830 and on identified location of the portable measurement system in the at least one image.

The identification of the portable measurement system in the image captured by the external camera may be executed in different ways. For example, the sensor may have a unique form factor. Optionally, a light source on the sensor (e.g. a LED or its UI screen) may emit a temporally recognizable pattern (e.g. a modulated throbbing signal), a graphic pattern, or even a pattern selected in order to distinguish itself from the rest of the scene (different in colors, in spatial formations, in temporal frequencies, etc.). The pattern emitted by the portable measurement system may be based on command issued by the external camera (or a system such as system 290). For example, the external camera may issue On/Off instructions, and identify the response of the portable measurement system.

The location criterion may be stated in pixels (e.g. less than 40 pixels between the portable measurement system and the examination location), in centimeters (e.g. less than 4 cm between this locations), or in any other way. The location criterion may change depending on the type of physiological measurement which is to be executed at the examination location. Other criterions (e.g. orientation of the sensor, battery level, signal level) may also be required before triggering the collection of the physiological measurement of stage 860.

Stage 850 may include stage 851 of showing to the patient indications of the examination locations (based on the locations indications) on the real time image/video (of herself) captured by the external camera, and/or on the reference image (or image which is based on the reference image). For example, stage 851 may include drawing a circle over the next examination location to be measured. This circle may move with the image of the patient, if the patient moves or changes postures. Stage 851 may include also emphasizing the location of the portable measurement system (e.g. by overlaying a graphic symbol over its location in the image), but this is not necessarily so.

This way, the patient can have a clear visible instruction on how to position the sensor correctly, for a successful physiological measurement. Optionally, the location to which the sensor should be brought may be marked using a first graphical representation, and the current location of the sensor can be marked using a second graphical representation. Optionally, the first and second graphical representations are designed to complete each other (e.g. two halves of a circle, a cross-shaped frame and a smaller cross fitting inside it, and so on). Optionally, a third graphical representation may be presented once the portable measurement system is in its designated location (e.g. a green circle). It is noted that the second graphical representation may be omitted.

The acquisition of physiological data by the portable measurement system may be triggered once the condition of stage 850 is fulfilled, but other triggering schemes may also be implemented. For example, the physiological measurement may start even before the fulfillment of the condition of stage 850, and upon the condition a marker may be added to the physiological data (or to the image data recorded by the external camera), or any other action can be made (e.g. instructing the patient as to further actions).

Stage 860 of method 800 includes recording physiological measurement data received from the portable measurement system. Stage 860 may be triggered by the external camera (or a system in which it is included or which is connected thereto), by the sensor, or by a remote system (such as a server). Optionally, the triggering may be based on inputs of the patient. Optionally, the triggering may be based on physiological measurement data received from the sensor (e.g. when a signal of sufficient quality is sampled). Optionally, the triggering may be based on relative locations between the sensor and the designated measurement location (e.g. even when the sensor is close but not quite at the right location). Additional information regarding to the triggering is presented with respect to stage 505 of method 500, and is relevant for stage 860 mutatis mutandis.

Stage 860 may be initiated upon a fulfilment of the condition of stage 850, but this is not necessarily so, and other triggering conditions may be used. Other scenarios may include triggering the collection of the physiological measurement by the remote medical expert, local triggering by the user, and so on.

Optionally, upon a fulfilment of the condition of stage 850, stage 870 is executed, which includes acquiring (and/or marking) the positioning image by the external camera. Other scenarios for triggering of stage 870 may include triggering by the remote medical expert, local triggering by the user, and so on.

Stage 870 may include executing stage 520 of method 500, and any information provided above with respect to stage 520 may be implemented, mutatis mutandis, with respect to stage 870. The term "positioning image" is discussed in details above.

Stages 860 and 870 are followed by stage 880 of synchronizing (or otherwise associating) the positioning image and the physiological measurement. Stage 880 may include executing stage 530 of method 500, and any information provided above with respect to stage 530 may be implemented, mutatis mutandis, with respect to stage 880. For example, stage 880 may include adding a time stamp to the physiological record and/or to the positioning image. In another example, stage 880 may include adding a measurement identifier (e.g. a unique identifier) to the physiological record and to the positioning image.

Stage 880 may be optionally be followed by executing any combination of one or more of stages 891, 892 and 893, which correspond to stages 540, 550 and 560 of method 500 (respectively). Any information provided above with respect to stage 540, 550 or 560 may be implemented, mutatis mutandis, with respect to stage 891, 892 or 893 (respectively).

Method 800 may also include stage 8100 of applying correction actions if one or more of the conditions of stages 840 and 850 is no longer fulfilled. For example—such scenarios may include: the patient moved away from the posture of the reference image; the patient moved the portable measurement system away from the designated examination location (or changed it orientation or pressure level, if relevant); the signal quality of the physiological measurement fell below a quality threshold, and so on.

Few correction actions which may be executed in response to such occasion may include, for example, any one or more of the following: instructing the patient to resume correct operation; stopping the recording of the physiological measurement; marking a time in which the occurrence happened in the physiological record; acquiring a positioning image, and so on.

It is noted that similar troubleshooting procedures (like stage 8100) may also be incorporated to method 500 as well.

If more than one examination location is required during an examination process of the user, stage 850 may be repeated, together with following stages as discussed above. It is noted that different requirements may need to be fulfilled, before another instance of stage 850 is executed. For example, a successful execution of stage 860, 870 and/or 880 may need to be verified before starting another instance of stage 850.

As aforementioned, optionally, method 800 may be executed by system 200. Optionally, system 200 may include image processing module (not illustrated) which is operable to process the positioning image to provide the orientation image, wherein the processing includes anonymizing the orientation image for removing identifiable visual information from the orientation image. The anonymization executed by the image processing module may include any one or more of the anonymization techniques discussed with respect to method 800.

It is noted that the image processing module may be part of processor 250, but not necessarily so. The imaging processor module may be the same image processing module which process positioning images to provide orientation images in which the portable measurement system is shown, as discussed above.

Referring to method 500, it is noted that it may include any one or more stages of method 800, or variations thereof. For example, method 500 may include processing at least one image acquired by the external camera to determine whether a location of the portable measurement system in the at least one image with respect to a predetermined location fulfils a proximity criterion (e.g. similarly to stage 850), and selectively triggering collection of the physiological measurement measured by the portable measurement system, upon a condition in which the location fulfils the proximity criterion. As discussed with respect to stages 850, 860 and 870, the triggering of the collection of the physiological measurement may include triggering an initiation of the measurement, triggering recording of the measurement, and/or triggering transmission of the measurement to the remote system.

The proximity criterion may be stated in pixels (e.g. less than 40 pixels between the sensor and the predetermined location), in centimeters (e.g. less than 4 cm between this locations), or in any other way. The proximity criterion may change depending on the type of physiological measurement which is to be executed at the predetermined location. Other criterions (e.g. orientation of the sensor, battery level, signal level) may also be required before triggering the collection of the physiological measurement.

With respect to system 200, this may be implemented by system 200 including: (a) an image processing module which is operable to process at least one image acquired by the external camera to determine whether a location of the portable measurement system in the at least one image with respect to a predetermined location fulfils a proximity criterion; and (b) a processor operable to selectively trigger collection of the physiological measurement measured by the portable measurement system, upon a condition in which the location fulfils the proximity criterion. It is noted that the image processing module may be part of processor 250, but not necessarily so. The imaging processor module may be the same image processing module which process positioning images to provide orientation images in which the portable measurement system is shown, as discussed above.

In another example, method 500 may include processing at least one image acquired by the external camera to determine whether a location of the portable measurement system in the at least one image with respect to a predetermined location fulfils a proximity criterion (e.g. similarly to stage 850), and selectively providing a UI indication to the user (e.g. a sound, a graphical representation) indicating that the portable physiological sensor is positioned well, upon a condition in which the location fulfils the proximity criterion.

The proximity criterion may be stated in pixels, in centimeters, or in any other way. The proximity criterion may change depending on the type of physiological measurement which is to be executed at the predetermined location. Other criterions (e.g. orientation, battery level, signal level) may also be required before triggering the UI indication.

System 400 and method 600 may be adapted for supporting examination locations selected by a physician, a technician, a medical expert, or any other user remote from system 200.

Physiological monitoring system 400, for example, may have its communication module 410 operable to receive the plurality of physiological measurement records, the plurality of visible light orientation images and the association data from a remote system (in this case, system such as system 200) which includes: a portable measurement system which acquires the physiological measurement and a camera external to the portable measurement system which acquired images of the body of the patient.

A user interface of system 400 (including modules 440 and 450) may be configured to: (a) display a reference image of the body of the patient acquired by the camera, and (b) obtain user inputs indicating a plurality of user-selected locations on the reference image. Communication module 410 in such case is operable to transmit to the remote system (e.g. system 200) information indicative of the user-selected locations; wherein the plurality of physiological measurements are acquired at different positions which are determined by the remote system based on the user-selected location.

With respect to method 600, the receiving of stage 610 may include receiving the plurality of physiological measurement records, the plurality of visible light orientation images and the association data from a remote system which includes a portable measurement system which acquires the physiological measurement and a camera external to the portable measurement system which acquired images of the body of the patient. The receiving of stage 610 may also be preceded by:
  a. displaying on a user interface a reference image of the body of the patient acquired by the camera;
  b. obtaining user inputs indicating a plurality of user-selected locations on the reference image;
  c. transmitting to the remote system information indicative of the user-selected locations;

In such a case, the plurality of physiological measurements may be such which acquired at different positions which are determined by the remote system based on the user-selected location.

Figure 16:
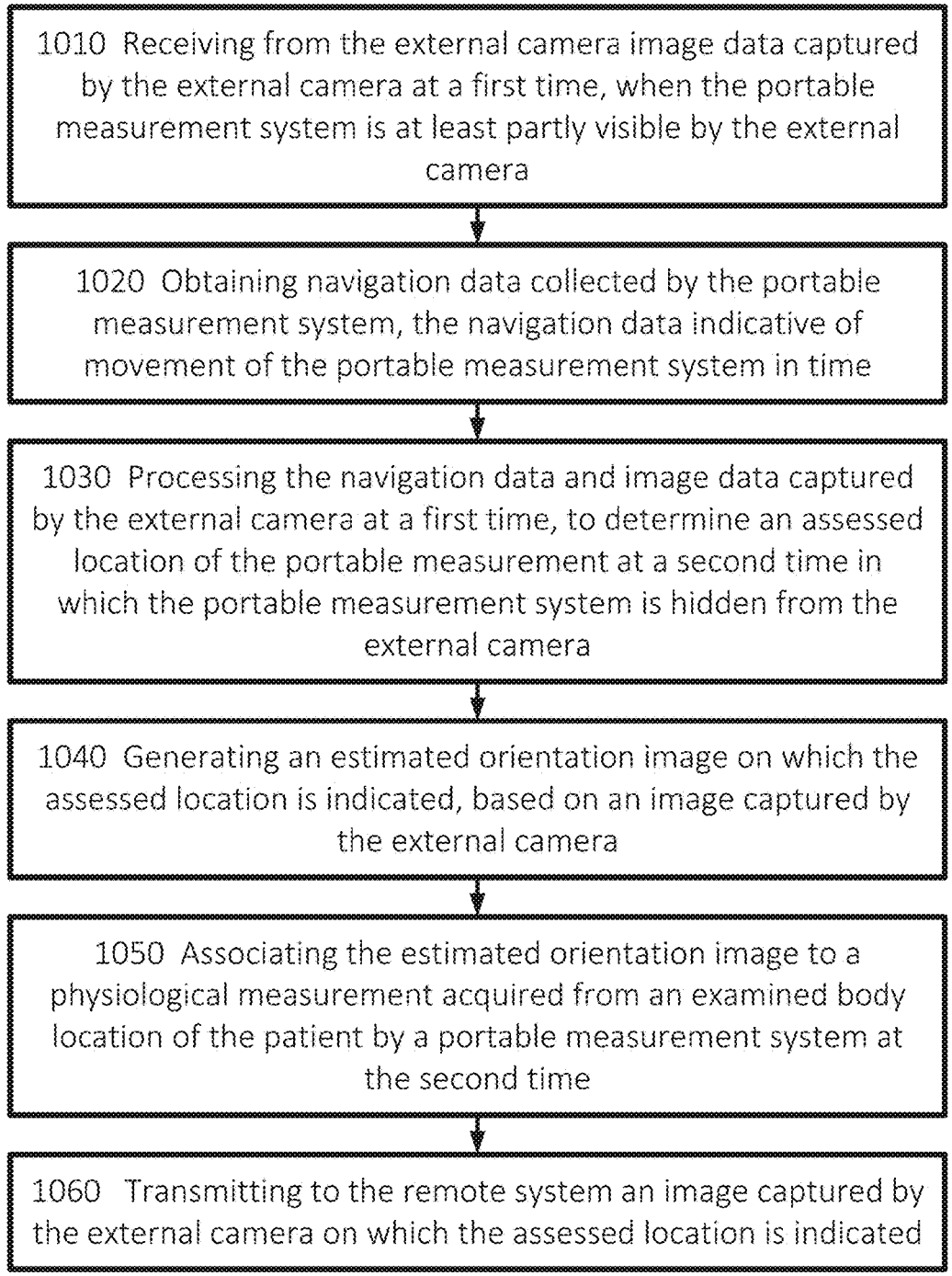
FIG. 16 is a flow chart illustrating an example of a computer-implemented method for determining a position of a portable measurement system while it is hidden from the external camera, in accordance with the presently disclosed subject matter.

FIG. 16 is a flow chart illustrating an example of a computer-implemented method 1000 for determining a position of a portable measurement system while it is hidden from the external camera, in accordance with the presently disclosed subject matter. Referring to the examples set forth with respect to the previous drawings, method 800 may be executed using system 200. It is noted that method 1000 may also be incorporated into method 500.

Method 1000 includes stage 1010 of receiving from the external camera image data captured by the external camera at a first time, when the portable measurement system is at least partly visible by the external camera (and its location can therefore be determined).

Stage 1020 includes obtaining navigation data collected by the portable measurement system, the navigation data indicative of movement of the portable measurement system in time. Especially, the navigation data is indicative of movement of the portable measurement system after the first time. The navigation data may be obtained by inertial sensors, by gyroscopes, and so on—of the portable measurement system. Stage 1020 is executed by the unit which executes stage 1030 (e.g. processor 250, synchronization module 230, and so on).

Stage 1030 includes processing the navigation data and image data captured by the external camera at a first time, to determine an assessed location of the portable measurement at a second time in which the portable measurement system is hidden from the external camera. For example, the second time may be 1-60 seconds later than the first time (or longer). It is noted that the user may be requested to show the portable measurement system to the external camera once in a while, to prevent large errors from accumulating.

Method 1000 may include stage 1040 of generating an estimated orientation image on which the assessed location is indicated, based on an image captured by the external camera.

Method 1000 may include stage 1050 of associating the estimated orientation image to a physiological measurement acquired from an examined body location of the patient by a portable measurement system at the second time. Stage 1050 may include associating image and physiological data similarly to the associating of stage 530 of method 500, and any information provided above with respect to stage 530 may be implemented, mutatis mutandis, with respect to stage 1050.

Stage 1060 of method 1000 includes transmitting to the remote system an image captured by the external camera on which the assessed location is indicated. The assessed location may be represented by any graphical symbol, or any other graphical representation.

Method 1000 may be used (either together with method 500, or separately of which), for example, in order to enable physiological measurements in areas which are not visible to the external camera, without requiring the patient to change position. For example, if the sensor is a camera which takes images of moles of the patient, moles on the front part of the body of the patient may be imaged with the position of the sensor recorded by executing method 500, while moles on the back may be recorded by executing method 1000. Like in methods 500 and 800, method 1000 may also include recording and transmitting of additional parameters such as orientation of the sensor, filters, and so on.

It is noted that in addition to movement sensors, 3D reconstruction may also be used to detect the positioning of the sensor, by multiple external cameras.

It is noted that method 1000 may be executed by system 200. For example, optionally, system 200 may include an image processing module (not illustrated) which is operable to: (a) obtain navigation data collected by portable measurement system 210, and navigation data indicative of movement of the portable measurement system in time; (b) process the navigation data and image data captured by the external camera 220 at a first time, to determine an assessed location of the portable measurement at a second time in which the portable measurement system is hidden from the external camera; and (c) generate an estimated orientation image on which the assessed location is indicated, based on an image captured by the external camera 220.

It is noted that the image processing module may be part of processor 250, but not necessarily so. The imaging processor module may be the same image processing module which process positioning images to provide orientation images in which the portable measurement system is shown, as discussed above.

Synchronization module 230, in such case, is operable to associate to the estimated orientation image physiological measurement acquired at the second time, and communication module 240 is operable to transmit to the remote system: (a) a second physiological measurement record which is based on the physiological measurement acquired at the second time, (b) the estimated orientation image, and (c) association data associating the estimated orientation image and the second physiological measurement record.

Figure 17A:
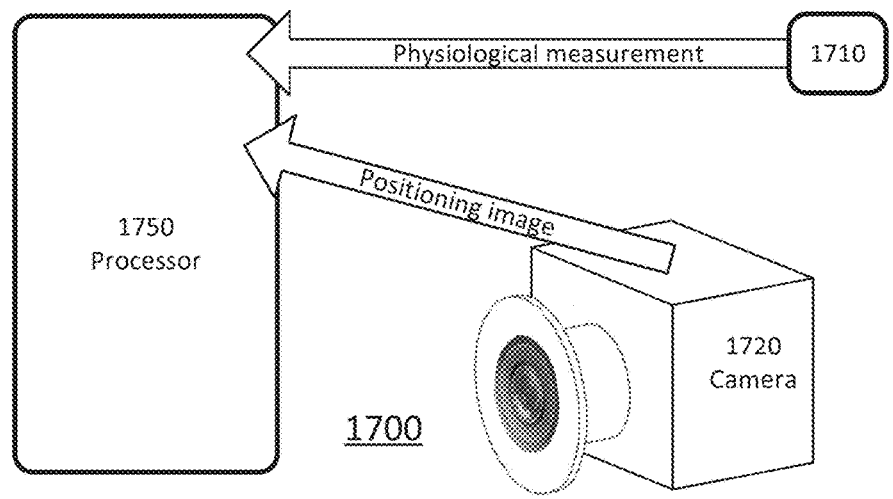
FIGS. 17A and 17B are functional block diagrams illustrating examples of a system for measuring physiological parameters of a patient, in accordance with the presently disclosed subject matter.
Figure 17B:
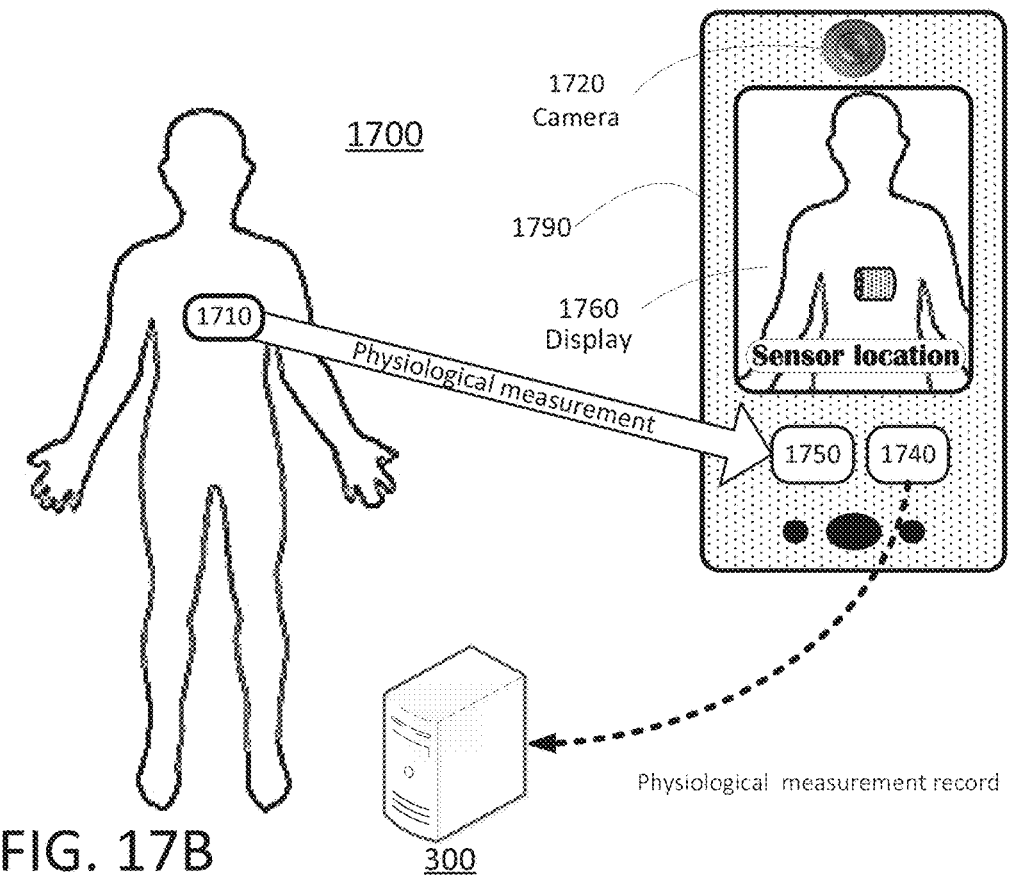

FIGS. 17A and 17B are functional block diagrams illustrating examples of system 1700 for measuring physiological parameters of a patient, in accordance with the presently disclosed subject matter. System 1700 includes at least:
 a. portable measurement system 1710, operable to acquire physiological measurement of the patient;
 b. external camera 1720, operable to capture visible light images of the body of the patient, oriented toward the examined body location; and
 c. processor 1750, operable to: (a) process at least one image acquired by the external camera to determine a location of the portable measurement system in the image at least one image; and (b) initiate a change in the physiological measurement of the portable measurement system upon a condition in which the location fulfils a proximity criterion with respect to a predetermined examination location.

It is noted that system 1700 may also serve as system 200 (in which case components 1710, 1720 and 1750 serve as components 210, 220 and 250, respectively), but this is not necessarily so. Any information provided above with respect to components 210, 220 or 250 may be implemented, mutatis mutandis, with respect to components 1710, 1720 or 1750 (respectively).

It is noted that processor 1750 may be operable to process multiple images of external camera 1720, but to determine the location of portable measurement system 1710 only in some of them (e.g. if system 1710 is not shown or identified in all of the images, or if only every N'th image is processed, etc.).

It is noted that processor 1750 may determine the location of the portable measurement system 1710 in several images of external camera 1720, but initiate a change in the physiological measurement only when the proximity criterion is fulfilled, and even than not in every case. For example, processor 1750 may initiate physiological measurement of system 1710 when it reaches a first distance from the predetermined examination location (e.g. 5 cm), to start recording the measurement information when system 1710 reaches to a second distance from the predetermined examination location (e.g. 2 cm), and to issue a UI notification to the user if system 1710 is moving away from the predetermined examination location (e.g. to a distance larger than 3 cm).

Optionally, processor 1750 may be operable to cause the portable measurement system 1710 to start the physiological measurement, upon the condition in which the location fulfils the proximity criterion.

Optionally, processor 1750 may be operable to cause initiation of collection of data of the physiological measurement, upon the condition in which the location fulfils the proximity criterion. For example, the collection of data may be executed by any one or more of the following: portable measurement system 1720, processor 1750, smartphone (or another portable computer such as a tablet computer) 1790, remote system 300, remote system 400. It is noted that the collection of the data of the physiological measurement may be accompanied by collection of additional data (e.g. images from external camera 1720, metadata relating to the measurement, tags, measurement serial numbers, other metadata, etc.).

Optionally, processor 1750 may be operable to cause portable measurement system 1710 to change a physiological measurement parameter, upon the condition in which the location fulfils the proximity criterion. For example, the changing of the physiological measurement parameter may include: measurement resolution, voltage levels, time differences between discrete measurements, and so on.

Optionally, processor 1750 may be operable is operable to cause a user interface to present an instruction to the user to modify the location of the portable measurement system, upon the condition in which the location fulfils the proximity criterion (e.g. if the patient moved the portable measurement system away from the designated examination location). The user interface may be, for example, display 1760, a speaker, or a UI of another system, such as a speaker of system 1710. Processor 1750 may also cause the user interface to present instructions or notifications in other conditions, if the patient changed the orientation and/or pressure level of system 1710, the signal quality of the physiological measurement fell below a quality threshold, by processing the reference image (e.g. to determine whether the patient changed her posture), and so on. The patient may be instructed to resume correct operation; or to move system 1710 to the correct location. Other actions which may be triggered by processor in such case are stopping the recording of the physiological measurement; marking a time in which the occurrence happened in the physiological record; acquiring a positioning image, and so on.

System 1700 may also include a communication module 1740 in order to transmit the physiological measurement to another system (e.g. in another location, such as a server, a call center, a medical clinic, etc.). The other system may be for example a remote desktop computer, a remote personal computer (e.g. laptop, tablet computer, smartphone), a server, system 300, system 400. Any information provided above with respect to communication module 240 may be implemented, mutatis mutandis, with respect to optional communication module 1740.

Reverting to FIG. 7, it is noted that system 1700 may be used at the patient location 100, where system 200 is illustrated. Also, the system used at the trained patient location 120 may be another system, which does not necessarily have all the capabilities of system 400 (e.g. it may not necessarily have to be operable to use synchronized data, as discussed with respect to system 400). Other changes and adjustments may also be implemented between the use of the systems of FIG. 7 and the use of system 1700.

FIG. 18 is a flow chart illustrating an example of computer-implemented method 1800 for physiological monitoring, in accordance with the presently disclosed subject matter. Referring to the examples set forth with respect to the previous drawings, method 1800 may be executed by system 1700.

Stage 1810 of method 1800 includes processing at least one visible light image showing a body of a patient and at list part of the portable measurement system to determine a location of the portable measurement system in the at least one image. Referring to the examples set forth with respect to the previous drawings, stage 1810 may be executed by external camera 1720.

The at least one visible light image may be acquired by a camera external to the portable measurement system, e.g. as discussed above with respect to the different methods and systems.

Stage 1820 of method 1800 includes initiating a new phase of a physiological measurement of the patient by the portable measurement system, upon a condition in which the location fulfils a proximity criterion with respect to a predetermined examination location.

For example, the initiating may include executing any one or more of the following actions:
a. Starting the physiological measurement.
b. Initiating collection of data of the physiological measurement.
c. Changing a physiological measurement parameter of the portable measurement system.
d. Initiating presentation of a user interface instruction to the user to modify the location of the portable measurement system.
e. Initiating presentation of another user interface instruction to the user.

It is noted that stages 1810 and 1820 may be repeated sequentially for different locations on the body of the patient, if one or more physiological examinations of the patient requires physiological measurements to be taken at different locations.

Figure 19A:
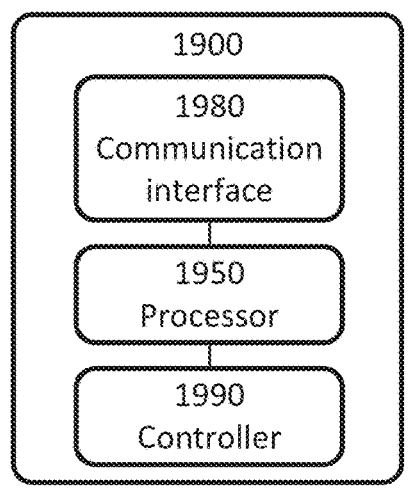
FIGS. 19A and 19B are functional block diagrams illustrating examples of a system for controlling measuring of physiological parameters of a patient, in accordance with the presently disclosed subject matter.
Figure 19B:
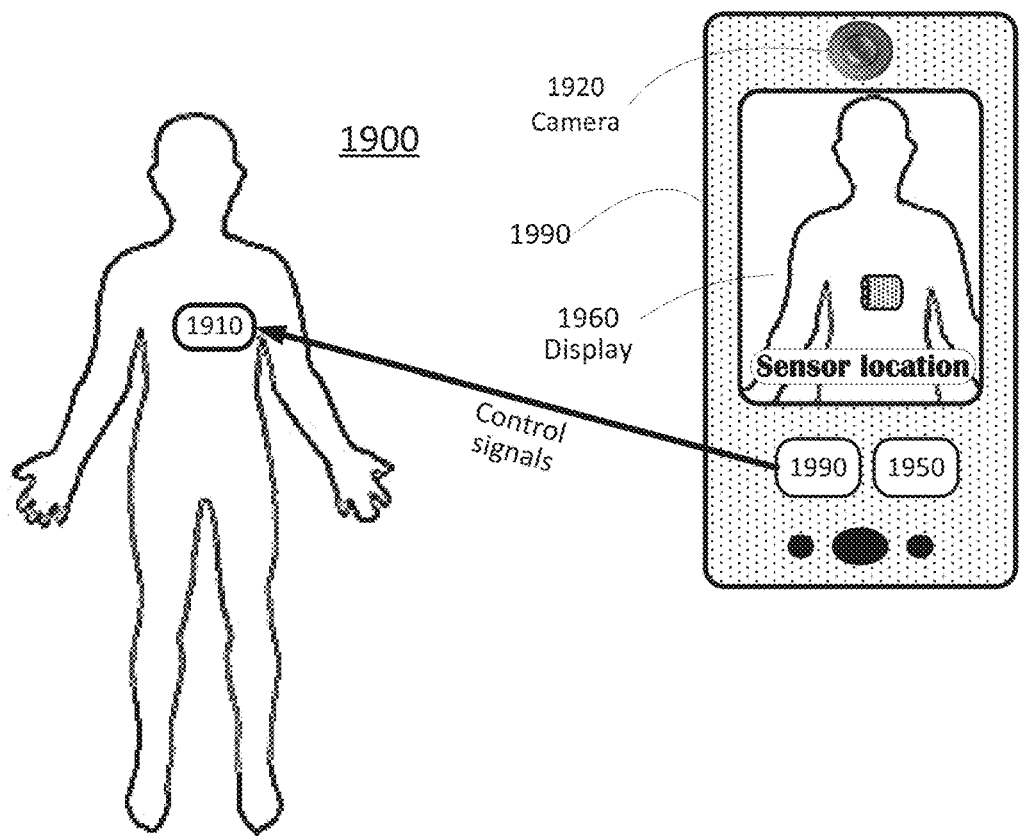

FIGS. 19A and 19B are functional block diagrams illustrating examples of system 1900 for controlling measuring of physiological parameters of a patient, in accordance with the presently disclosed subject matter. System 1900 includes at least communication interface 1980, processor 1950 and controller 1990.

Communication interface 1980 is operable to receive at least one examination location, which is defined with respect to a reference image which includes (i.e. shows) at least a part of a body of a patient.

Optionally, the examination location may be selected by a person (e.g. marked by a person on the reference image). This may be executed on a UI of system 1900, or on a remote system.

Optionally, the examination location may be selected using an automated algorithm, based on the reference image. For example, the automated algorithm may identify specific body parts (e.g. the eyes, the fingers) in the reference image, and determine the at least one examination location based on the identified body parts. In another example, the automated algorithm may compare the reference image to another image of the patient (e.g. in order to follow-up on a previous medical condition of the patient) and/or another image (e.g. exemplifying a medical condition), in order to determine the at least one examination location. In another example, the automated algorithm may process the reference image to identify specific physiological conditions (e.g. skin discolorations, scar tissue, mole, etc.), and determine the at least one examination location based on the identification. The automated algorithm may be executed by processor 1950, but may also be executed on a remote system.

Optionally, the communication interface may be an interface to a UI (e.g. to a touchscreen, computer mouse, etc.). Optionally, the communication interface may be an interface to a remote system (e.g. USB connection, wireless connection).

processor 1950 is operable at least to:
a. Process at least one examination location marked by a person on a reference image which includes (i.e. shows) at least a part of a body of a patient. The reference image is a visible light image acquired by an external camera (external to the portable measurement system which is controlled by controller 1990).
b. Determine positioning parameters for the portable measurement system based on a result of the processing.

The positioning parameters may be determined with respect to the reference image (e.g. defined in pixels, e.g. the portable measurement system should be positioned for the physiological measurement in the area defined by corner pixels (940, 500) and (960, 520)), with respect to the body of the patient (e.g. the portable measurement system should be positioned for the physiological measurement in a location defined with respect to identifiable body locations such as the eyes), with respect to another identifiable object (e.g. two electrodes should be positioned at a distance not larger than 7 cm between them), and so on.

The positioning parameters may change depending on the type of physiological measurement which is to be executed at the examination location. Other criterions (e.g. orientation of the sensor, battery level, signal level) may also be required before triggering the collection of the physiological measurement of stage 860.

It is noted that system 1910 may include a user interface (e.g. touch screen 1960) for displaying the reference image to the person and for receiving the person's marking of the at least one examination location. However, this is not necessarily so, and the user interface may be implemented on another system (e.g. system 400 or another system operated by a medical expert, e.g. at a remote location).

Controller 1990 is operable to control execution of a physiological measurement of the patient by the portable measurement sensor, based on the positioning parameters. The controller may be connected to processor 1950 (as exemplified in FIG. 19A), but may also be located elsewhere (e.g. as part of the portable measurement system).

System 1900 may include the portable measurement system and/or the external camera, but this is not necessarily so. Optionally, system 1900 may be implemented on a smartphone or a tablet computer, where the camera of the smartphone or tablet may serve as the external camera. Optionally, system 1900 may be integrated into a computer which also includes the external camera.

System 1900 may also include a memory for storing the positioning parameters for multiple uses. For example, a medical expert (or another user) may mark one or more examination locations on a reference image at one occurrence, and controller 1990 may control different measurements of physiological parameters for the patient at different times (e.g. at different days) by the portable measurement system, using the same positioning parameters.

Optionally, controller 1990 may be operable to control the execution of the physiological measurement based on the positioning parameters and on the reference image. This may be implemented, for example, similarly to any one of the controls discussed with respect to system 1700.

Optionally, processor 1950 may be operable to determine different positioning parameters based on a plurality of examination locations marked on the reference image by at least one person, and controller 1990 may be operable to control execution of a plurality of physiological measurements of the patient by the portable measurement system based on the different positioning parameters. Optionally, in such a case, controller 1990 may be further operable to control breaks between the plurality of physiological measurements based on the different positioning parameters (e.g. to measure physiological measurement such as temperature or collecting sounds, only when the portable measurement system is at predefined interesting positions, but not when the patient moves the portable measurement system between the locations).

As discussed above with respect to other systems, the patient may receive instructions on where to position the portable measurement system based on the positioning parameters, either on a UI of system 1900 (e.g. display 1960), or on a UI of another system.

Optionally, controller 1990 may be operable to control initiation of the physiological measurement based on the positioning parameters (e.g. as discussed with respect to system 1700 and to the proximity criterion, mutatis mutandis).

Optionally, controller 1990 may be operable to control initiation of collection of data of the physiological measurement based on the positioning parameters (e.g. as discussed with respect to system 1700 and to the proximity criterion, mutatis mutandis).

Optionally, controller 1990 may be operable to control changing of a physiological measurement parameter of the portable measurement system (e.g. as discussed with respect to system 1700 and to the proximity criterion, mutatis mutandis).

Optionally, controller 1990 may be operable to control presentation of a user interface instruction to the user to modify the location of the portable measurement system (e.g. as discussed with respect to system 1700, mutatis mutandis).

Optionally, processor 1950 may be further operable to process at least one visible light image showing the body of the patient and the portable measurement system which is acquired by the external camera after the determination of the positioning parameters, to determine a location of the portable measurement system in the at least one image. Controller 1990 in such a case may be operable to control initiation of a new phase of a physiological measurement of the patient by the portable measurement system, upon a condition in which the location fulfils a proximity criterion with respect to a predetermined examination location.

The initiation of the new phase may include, for example, any one of the following:

a. Initiating collection of data of the physiological measurement.
b. Changing a physiological measurement parameter of the portable measurement system.
c. Initiating presentation of a user interface instruction to the user to modify the location of the portable measurement system.

Reverting to FIG. 7, it is noted that system 1900 may be used at the patient location 100, where system 200 is illustrated. Also, the system used at the trained patient location 120 may be another system, which does not necessarily have all the capabilities of system 400 (e.g. it may not necessarily have to be operable to use synchronized data, as discussed with respect to system 400). Other changes and adjustments may also be implemented between the use of the systems of FIG. 7 and the use of system 1900.

FIG. 20 is a flow chart illustrating an example of computer-implemented method 2000 for physiological monitoring, in accordance with the presently disclosed subject matter. Referring to the examples set forth with respect to the previous drawings, method 2000 may be executed by system 1900.

Method 2000 may start with optional stage 2010 which includes acquiring a reference image which includes and at least a part of a body of a patient. The reference image is a visible light image acquired by an external camera external to the portable measurement system of stage 2040 (discussed below). Referring to the examples set forth with respect to the previous drawings, stage 2010 may be executed by processor 1950.

Stage 2020 of method 2000 includes obtaining at least one examination location which is defined with respect to a reference image which includes at least a part of a body of a patient. Optionally, the at least one examination location is marked by a person on the reference image. Optionally, the at least one examination location is determined by an automated algorithm. Optionally, the at least one examination location is determined by an automated algorithm combined with inputs of a person (e.g. a medical expert). Several examples to the determining of the at least one examination location were provided above with respect to system 1900.

Referring to the examples set forth with respect to the previous drawings, stage 2020 may be executed by Communication interface 1980, by processor 1950, and/or by a user interface (e.g. 1960), or any combination thereof. Method 2000 may include displaying the reference image on a user interface for the person, but this is not necessarily so as the marking may also be executed on another system.

Stage 2030 includes determining positioning parameters for the portable measurement system, based on the at least one examination location. Referring to the examples set forth with respect to the previous drawings, stage 2030 may be executed by processor 1950. Optionally, stage 2030 may include determining the positioning parameters based on the at least one examination location and on the reference image.

Stage 2040 includes controlling execution of a physiological measurement of the patient by the portable measurement sensor, based on the positioning parameters. Referring to the examples set forth with respect to the previous drawings, stage 2040 may be executed by controller 1990. Optionally, the controlling of stage 1990 may be further based on the reference image, and/or on addition parameters.

Optionally, stage 2020 may include includes obtaining a plurality of examination locations marked by at least one person, stage 2030 may include determining different positioning parameters based on the different examination locations, and stage 2040 may include controlling execution of a plurality of physiological measurements of the patient by the portable measurement system. In such case, method 2000 may further include controlling breaks between the plurality of physiological measurements based on the different positioning parameters.

a. The controlling of stage 2040 may include any one or more of the following:
b. controlling initiation of the physiological measurement.
c. initiating collection of data of the physiological measurement.
d. changing a physiological measurement parameter of the portable measurement system.
e. controlling presentation of a user interface instruction to the user to modify the location of the portable measurement system.
f. processing at least one visible light image, acquired by the external camera after the determining, the at least one visible image showing the body of the patient and the portable measurement system to determine a location of the portable measurement system in the at least one image; and initiating a new phase of physiological measurement of the patient by the portable measurement system, upon a condition in which the location fulfils a proximity criterion with respect to a predetermined examination location.

The invention may also be implemented in a computer program for running on a computer system, at least including code portions for performing steps of a method according to the invention when run on a programmable apparatus, such as a computer system or enabling a programmable apparatus to perform functions of a device or system according to the invention. Such methods include methods 500, 600 700, 1800 and 200 discussed above.

A computer program is a list of instructions such as a particular application program and/or an operating system. The computer program may for instance include one or more of: a subroutine, a function, a procedure, a method, an implementation, an executable application, an applet, a servlet, a source code, code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

What is claimed is:

1. A system for measuring physiological parameters of a patient, the system comprising:
   a portable measurement system, operable to acquire physiological measurement from an examined body location of the patient;
   an external camera, external to the portable measurement system, movable irrespective of the portable measurement system, and operable to capture visible light, oriented toward the examined body location;
   a synchronization module, operable to receive a triggering indication, and in response to the triggering indication to associate to the physiological measurement a positioning image captured by the external camera, the positioning image comprising at least a part of the portable measurement system adjacent to the examined body location; and
   a communication module operable to obtain the physiological measurement and the positioning image, and to transmit to a remote system:
   a physiological measurement record which is based on the physiological measurement,
   an orientation image which is based on the positioning image, the orientation image comprising at least a part of the portable measurement system adjacent to the examined body location, and
   association data associating the orientation image and the physiological measurement record.

2. The system according to claim 1, wherein the synchronization module is operable to trigger the measurement of the physiological measurement by the portable measurement system, and to control a creation of the positioning image.

3. The system according to claim 1, wherein the physiological measurement is a location sensitive physiological measurement whose medical interpretation necessitate information of location of measurement.

4. The system according to claim 1, wherein the portable measurement system comprises a microphone, operable to acquire the physiological measurement which comprises internal sounds of a body of the patient.

5. The system according to claim 1, wherein the portable measurement system comprises an ultrasonic transducer which is operable to acquire the physiological measurement which comprises ultrasonic sound waves reflected from a body of the patient.

6. The system according to claim 1, wherein the portable measurement system comprises a blood flow sensor, operable to acquire the physiological measurement which is indicative of at least one blood flow parameter.

7. The system according to claim 1, wherein the synchronization module is integrated with the portable measurement system.

8. The system according to claim 1, further comprising a user interface which is operable to transmit to the synchronization module an interaction indication upon identification of a human interaction with the user interface which satisfy at least one predetermined interaction criterion, wherein the synchronization module is operable to trigger the measurement of the physiological measurement by the portable measurement system in response to the interaction indication.

9. The system according to claim 1, further comprising a monitor operable to display to a user positioning instructions indicating a body location for measurement.

10. The system according to claim 1, wherein the portable measurement system is operable to acquire physiological measurements from a plurality of examined body locations of the patient; wherein the synchronization module is operable to associate to each physiological measurement out of the plurality of physiological measurements a corresponding positioning image captured by the external camera; wherein the communication module is operable transmit to the remote system: physiological measurement record corresponding to each physiological measurement out of the plurality measurements, a plurality of orientation images which are based on the positioning images, and association data associating each orientation image and the corresponding physiological measurement record.

11. The system according to claim 1, wherein the synchronization module is operable to receive multiple triggering indications during a continuous physiological examination, and in response to each of the multiple triggering indications to associate a positioning image to the physiological measurement measured during the continuous physiological examination.

12. The system according to claim 1, wherein the positioning image is selected from a sequence of images captured by the external camera comprising a plurality of images.

13. The system according to claim 1, further comprising an image processing module, operable to: (a) obtain navigation data collected by the portable measurement system, and navigation data indicative of movement of the portable measurement system in time; (b) process the navigation data and image data captured by the external camera at a first time, to determine an assessed location of the portable measurement at a second time in which the portable measurement system is hidden from the external camera; and (c) generate an estimated orientation image on which the assessed location is indicated, based on an image captured by the external camera;

wherein the synchronization module is operable to associate to the estimated orientation image the physiological measurement acquired at the second time;

wherein the communication module is operable to transmit to the remote system: (a) a second physiological measurement record which is based on the physiological measurement acquired at the second time, (b) the estimated orientation image, and (c) association data associating the estimated orientation image and the second physiological measurement record.

14. The system according to claim 1, comprising an image processing module which is operable to process the positioning image to provide the orientation image, wherein the processing comprises anonymizing the orientation image for removing identifiable visual information from the orientation image.

15. The system according to claim 1, comprising an image processing module which is operable to process at least one image acquired by the external camera to determine whether a location of the portable measurement system in the at least one image with respect to a predetermined location fulfils a proximity criterion; and a processor operable to selectively trigger collection of the physiological measurement measured by the portable measurement system, upon a condition in which the location fulfils the proximity criterion.

16. The system according to claim 1, further comprising an image processing module operable to process the positioning image to identify a location of the portable positioning system within the positioning image, wherein the communication module is operable to transmit to the remote system information indicative of the location of the portable positioning system within the positioning image.

17. A physiological monitoring system, the system comprising:
a communication module operable to receive:
a plurality of physiological measurement records of a plurality of physiological measurements acquired by a portable measurement system at different positions of the portable measurement system with respect to a body of a patient,
a plurality of visible light orientation images, acquired by an external camera, external to the portable measurement system and movable irrespective of the portable measurement system, each of the plurality of visible light orientation images being indicative of a location of a portable measurement system with respect to the body of the patient, and
association data associating each orientation image with a corresponding physiological measurement record out of the plurality of physiological measurement records;
a processor, operable to process the association data and to retrieve from a physiological measurements database, based on results of the processing: (a) a selected physiological measurement record and (b) at least one matching orientation image; and
a user interface output configured to display the at least one matching orientation image in combination with providing information of the selected physiological measurement record.

18. The physiological monitoring system according to claim 17, wherein the physiological measurements are location sensitive physiological measurements whose medical interpretation necessitate information of location of measurement.

19. The physiological monitoring system according to claim 17, wherein the user interface output is configured to display a plurality of orientation images associated with different physiological measurement records; wherein the physiological monitoring system further comprises a user interface input for receiving a selection indication, indicative of an orientation image out of the plurality of orientation images; wherein the processor is operable to retrieve the selected physiological measurement records based on the selection indication.

20. The physiological monitoring system according to claim 17, wherein the user interface output is configured to display identifiers of a plurality of physiological measurement records; wherein the physiological monitoring system further comprises a user interface input for receiving a selection indication, indicative of physiological measurement record out of the plurality of physiological measurement records; wherein the processor is operable to retrieve the selected physiological measurement records based on the selection indication.

21. The physiological monitoring system according to claim 17, wherein the user interface output is operable to display a video which comprises the plurality of orientation images, wherein the processor is operable to retrieve from the physiological measurements database the physiological measurement records, and to synchronize providing information of the different physiological measurement records with the displaying of the video, based on the association data.

22. The physiological monitoring system according to claim 17, wherein the communication module receives the plurality of physiological measurement records, the plurality of visible light orientation images and the association data from a remote system which comprises: a portable measurement system which acquires the physiological measurement and a camera external to the portable measurement system which acquired images of the body of the patient; wherein the physiological monitoring system further comprises a user interface configured to: (a) display a reference image of the body of the patient acquired by the camera, and (b) obtain user inputs indicating a plurality of user-selected locations on the reference image; wherein the communication module is operable to transmit to the remote system information indicative of the user-selected locations; wherein the plurality of physiological measurements are acquired at different positions which are determined by the remote system based on the user-selected location.

23. A system for measuring physiological parameters of a patient, the system comprising:
a portable measurement system, operable to acquire physiological measurement of the patient;
an external camera, external to the portable measurement system, movable irrespective of the portable measurement system, and operable to capture visible light images of the body of the patient;

a processor, operable to:
  process at least one image acquired by the external camera to determine a location of the portable measurement system in the image; and
  initiate a change in the physiological measurement of the portable measurement system upon a condition in which the location fulfils a proximity criterion with respect to a predetermined examination location.

24. The system according to claim 23, wherein the processor is operable to cause the portable measurement system to start the physiological measurement, upon the condition in which the location fulfils the proximity criterion.

25. The system according to claim 23, wherein the processor is operable to cause initiation of collection of data of the physiological measurement, upon the condition in which the location fulfils the proximity criterion.

26. The system according to claim 23, wherein the processor is operable to cause the portable measurement system to change a physiological measurement parameter, upon the condition in which the location fulfils the proximity criterion.

27. The system according to claim 23, wherein the processor is operable to cause a user interface to present an instruction to the user to modify the location of the portable measurement system, upon the condition in which the location fulfils the proximity criterion.

28. A system for controlling measuring of physiological parameters of a patient, the system comprising:
  a communication interface operable to receive at least one examination location, wherein the at least one examination location is defined with respect to a reference image which comprises at least a part of a body of a patient;
  a processor, operable to process the at least one examination location, and to determine positioning parameters for a portable measurement system based on a result of the processing; and
  a controller, operable to control execution of a physiological measurement of the patient by the portable measurement system, based on the positioning parameters;
  wherein the reference image is a visible light image acquired by an external camera which is external to the portable measurement system and movable irrespective of the portable measurement system.

29. The system according to claim 28, wherein the at least one examination location is marked by a person on the reference image.

30. The system according to claim 28, wherein the controller is operable to control the execution of the physiological measurement based on the positioning parameters and on the reference image.

31. The system according to claim 28, wherein the processor is operable to determine different positioning parameters based on a plurality of examination locations marked on the reference image by at least one person, wherein the controller is operable to control execution of a plurality of physiological measurements of the patient by the portable measurement system based on the different positioning parameters, and to control breaks between the plurality of physiological measurements based on the different positioning parameters.

32. The system according to claim 28, wherein the controller is operable to control initiation of the physiological measurement based on the positioning parameters.

33. The system according to claim 28, wherein the controller is operable to control initiation of collection of data of the physiological measurement based on the positioning parameters.

34. The system according to claim 28, wherein the controller is operable to control changing of a physiological measurement parameter of the portable measurement system.

35. The system according to claim 28, wherein the controller is operable to control presentation of a user interface instruction to the user to modify the location of the portable measurement system.

36. The system according to claim 28, wherein the processor is further operable to process at least one visible light image showing the body of the patient and the portable measurement system which is acquired by the external camera after the determination of the positioning parameters, to determine a location of the portable measurement system in the at least one image; wherein the controller is operable to control initiation of a new phase of a physiological measurement of the patient by the portable measurement system, upon a condition in which the location fulfils a proximity criterion with respect to a predetermined examination location.

37. A method for measuring physiological parameters of a patient, the method comprising:
  associating a positioning image to a physiological measurement acquired from an examined body location of the patient by a portable measurement system; the positioning image being an image captured by an external visible light camera, external to the portable measurement system and movable irrespective of the portable measurement system, the external visible light camera being oriented toward the examined body location, which comprises at least part of the portable measurement system adjacent to the examined body location; and
  transmitting to a remote system: a physiological measurement record which is based on the physiological measurement, an orientation image which is based on the positioning image and which comprises at least part of the portable measurement system adjacent to the examined body location, and association data associating the orientation image and the physiological measurement record.

38. The method according to claim 37, wherein the physiological measurement is a location sensitive physiological measurement whose medical interpretation necessitate information of location of measurement.

39. The method according to claim 37, further comprising acquiring the physiological measurement from the examined body location by the portable measurement system.

40. The method according to claim 37, wherein the physiological measurement comprises sounds of at least one lung of the patient.

41. The method according to claim 37, wherein the physiological measurement comprises ultrasonic sound waves reflected from a body of the patient.

42. The method according to claim 37, wherein the physiological measurement which is indicative of at least one blood flow parameter.

43. The method according to claim 37, further comprising selectively triggering the measurement of the physiological measurement by the portable measurement system in response to a user input which satisfy at least one predetermined interaction criterion.

44. The method according to claim 37, further comprising providing, via a user interface, positioning instructions indicating a body location for measurement.

45. The method according to claim 37, comprising:
acquiring physiological measurements from a plurality of examined body locations of the patient;
associating to each physiological measurement out of the plurality of physiological measurements a corresponding positioning image captured by the external camera; and
transmitting to the remote system: (a) physiological measurement record corresponding to each physiological measurement out of the plurality measurements, (b) a plurality of orientation images which are based on the positioning images, and (c) association data associating each orientation image and the corresponding physiological measurement record.

46. The method according to claim 37, comprising selecting the positioning image out of a sequence of images captured by the external camera, the sequence comprising a plurality of images.

47. The method according to claim 37, comprising:
obtaining navigation data collected by the portable measurement system, the navigation data indicative of movement of the portable measurement system in time;
processing the navigation data and image data captured by the external camera at a first time, to determine an assessed location of the portable measurement at a second time in which the portable measurement system is hidden from the external camera;
and transmitting to the remote system an image captured by the external camera on which the assessed location is indicated.

48. The method according to claim 37, wherein the transmitting is preceded by processing the positioning image to provide the orientation image, wherein the processing comprises anonymizing the orientation image for removing identifiable visual information from the orientation image.

49. The method according to claim 37, comprising:
processing at least one image acquired by the external camera to determine whether a location of the portable measurement system in the at least one image with respect to a predetermined location fulfils a proximity criterion; and
selectively triggering a collection of the physiological measurement measured by the portable measurement system, upon a condition in which the location fulfils the proximity criterion.

50. The method according to claim 37, further comprising processing the positioning image to identify a location of the portable positioning system within the positioning image, wherein the transmitting further comprises transmitting to the remote system information indicative of the location of the portable positioning system within the positioning image.

51. A computer-implemented method for physiological monitoring, the method comprising:
receiving:
a plurality of physiological measurement records of a plurality of physiological measurements acquired by a portable measurement system at different positions of the portable measurement system with respect to a body of a patient,
a plurality of visible light orientation images, acquired by an external camera, external to the portable measurement system and movable irrespective of the portable measurement system, each of the plurality of orientation images being indicative of a location of a portable measurement system with respect to the body of the patient, and
association data associating each orientation image with a corresponding physiological measurement record out of the plurality of physiological measurement records;
storing on a tangible memory: the plurality of physiological measurement records, the plurality of orientation images, and the association data;
based on the association data, retrieving from the tangible memory a selected physiological measurement record and at least one matching orientation image; and
displaying the at least one matching orientation image in combination with providing information of the selected physiological measurement record.

52. The method according to claim 51, comprising displaying a plurality of orientation images associated with different physiological measurement records; receiving a selection indication indicative of a selection by a user of at least one out of the plurality of orientation images; and retrieving the selected physiological measurement records based on the selection indication.

53. The method according to claim 51, comprising displaying identifiers of a plurality of physiological measurement records; receiving a selection indication indicative of selection by a user of a physiological measurement record out of the plurality of physiological measurement records; and retrieving the selected physiological measurement records based on the selection indication.

54. The method according to claim 51, comprising displaying a video which comprises the plurality of orientation images, retrieving from the tangible memory the physiological measurement records, and synchronizing providing information of the different physiological measurement records with the displaying of the video, based on the association data.

55. The method according to claim 51, wherein the receiving comprises receiving the plurality of physiological measurement records, the plurality of visible light orientation images and the association data from a remote system which comprises a portable measurement system which acquires the physiological measurement and a camera external to the portable measurement system which acquired images of the body of the patient; wherein the receiving is preceded by:
displaying on a user interface a reference image of the body of the patient acquired by the camera;
obtaining user inputs indicating a plurality of user-selected locations on the reference image;
transmitting to the remote system information indicative of the user-selected locations;
wherein the plurality of physiological measurements are acquired at different positions which are determined by the remote system based on the user-selected location.

56. A computer-implemented method for physiological monitoring, the method comprising:
processing at least one visible light image showing a body of a patient and a portable measurement system to determine a location of the portable measurement system in the at least one image, wherein the visible light image is acquired by an external camera, external to the portable measurement system and movable irrespective of the portable measurement system; and
initiating a new phase of a physiological measurement of the patient by the portable measurement system, upon a condition in which the location fulfils a proximity criterion with respect to a predetermined examination location.

57. The method according to claim 56, wherein the initiating comprises starting the physiological measurement.

58. The method according to claim 56, wherein the initiating comprises initiating collection of data of the physiological measurement.

59. The method according to claim 56, wherein the initiating comprises changing a physiological measurement parameter of the portable measurement system.

60. The method according to claim 56, wherein the initiating comprises initiating presentation of a user interface instruction to the user to modify the location of the portable measurement system.

61. A computer-implemented method for physiological monitoring, the method comprising:
   obtaining at least one examination location which is defined with respect to a reference image which comprises at least a part of a body of a patient;
   determining positioning parameters for a portable measurement system, based on the at least one examination location; and
   controlling execution of a physiological measurement of the patient by the portable measurement system, based on the positioning parameters;
   wherein the reference image is a visible light image acquired by an external camera external to the portable measurement system and movable irrespective of the portable measurement system.

62. The method according to claim 61, wherein the at least one examination location is marked by a person on the reference image.

63. The method according to claim 61, wherein the controlling is further based on the reference image.

64. The method according to claim 61, wherein the obtaining comprises obtaining a plurality of examination locations marked by at least one person, wherein the determining comprises determining different positioning parameters based on the different examination locations, wherein the controlling comprises controlling execution of a plurality of physiological measurements of the patient by the portable measurement system, wherein the method further comprises controlling breaks between the plurality of physiological measurements based on the different positioning parameters.

65. The method according to claim 61, wherein the controlling comprises controlling initiation of the physiological measurement.

66. The method according to claim 61, wherein the controlling comprises initiating collection of data of the physiological measurement.

67. The method according to claim 61, wherein the controlling comprises changing a physiological measurement parameter of the portable measurement system.

68. The method according to claim 61, wherein the controlling comprises controlling presentation of a user interface instruction to the user to modify the location of the portable measurement system.

69. The method according to claim 61, wherein the controlling comprises processing at least one visible light image, acquired by the external camera after the determining, the at least one visible image showing the body of the patient and the portable measurement system to determine a location of the portable measurement system in the at least one image; wherein the controlling comprises initiating a new phase of a physiological measurement of the patient by the portable measurement system, upon a condition in which the location fulfils a proximity criterion with respect to a predetermined examination location.

70. A non-transitory computer-readable medium for physiological monitoring, comprising instructions stored thereon, that when executed on a processor, perform the steps of:
   obtaining:
   a plurality of physiological measurement records of a plurality of physiological measurements acquired by a portable measurement system at different positions of the portable measurement system with respect to a body of a patient,
   a plurality of visible light orientation images, acquired by an external camera, external to the portable measurement system and movable irrespective of the portable measurement system, each of the plurality of orientation images being indicative of a location of a portable measurement system with respect to the body of the patient, and
   association data associating each orientation image with a corresponding physiological measurement record out of the plurality of physiological measurement records;
   storing on a tangible memory: the plurality of physiological measurement records, the plurality of orientation images, and the association data;
   based on the association data, retrieving from the tangible memory a selected physiological measurement record and at least one matching orientation image; and
   displaying the at least one matching orientation image in combination with providing information of the selected physiological measurement record.

* * * * *